United States Patent
Sperling et al.

(10) Patent No.: US 11,771,486 B2
(45) Date of Patent: Oct. 3, 2023

(54) DEVICE FOR ABLATION OF TISSUE SURFACES AND RELATED SYSTEMS AND METHODS

(71) Applicant: Corfigo, Inc., Montclair, NJ (US)

(72) Inventors: Jason Sperling, Upper Saddle River, NJ (US); Benjamin Cameron, Lyme, NH (US); John McCormick, Norwich, VT (US); Patrick Magari, Plainfield, NH (US); John VanScoy, Plymouth, MN (US); Robert Hudgins, Monticello, MN (US); John Dockter, Eden Prairie, MN (US)

(73) Assignee: Corfigo, Inc., Montclair, NJ (US)

( * ) Notice: Subject to any disclaimer, the term of this patent is extended or adjusted under 35 U.S.C. 154(b) by 397 days.

(21) Appl. No.: 15/873,606

(22) Filed: Jan. 17, 2018

(65) Prior Publication Data

US 2018/0206900 A1 Jul. 26, 2018
US 2019/0254731 A9 Aug. 22, 2019

Related U.S. Application Data

(60) Provisional application No. 62/596,239, filed on Dec. 8, 2017, provisional application No. 62/461,930, filed
(Continued)

(51) Int. Cl.
*A61B 18/02* (2006.01)
*A61B 18/14* (2006.01)
(Continued)

(52) U.S. Cl.
CPC .......... *A61B 18/02* (2013.01); *A61B 18/1492* (2013.01); *A61B 34/25* (2016.02);
(Continued)

(58) Field of Classification Search
CPC .. A61B 2018/00023; A61B 2018/0022; A61B 2018/00577; A61B 2018/0262;
(Continued)

(56) References Cited

U.S. PATENT DOCUMENTS 5,241,951 A * 9/1993 Mason ................ A61F 5/05816
607/104
5,383,919 A * 1/1995 Kelly ........................ A61F 7/02
601/15

(Continued)

FOREIGN PATENT DOCUMENTS

CN 107440782 A 12/2017
EP 3073931 A2 10/2016
(Continued)

*Primary Examiner* — Thomas A Giuliani
*Assistant Examiner* — Christine A Dedoulis
(74) *Attorney, Agent, or Firm* — Fredrikson & Byron, P.A.

(57) ABSTRACT

Provided herein are ablation systems having an ablation component with an ablation chamber and an insulation chamber, wherein the ablation chamber comprises a plurality of channels defined there. Other embodiments include ablation systems having a substrate source, a cooling component, and an ablation component. Certain systems are closed-loop systems that reuse the cooling substrate.

20 Claims, 24 Drawing Sheets

Related U.S. Application Data on Feb. 22, 2017, provisional application No. 62/446,976, filed on Jan. 17, 2017.

(51) Int. Cl.

| | | |
|---|---|---|
| *A61B 34/00* | (2016.01) | |
| *A61B 17/00* | (2006.01) | |
| *A61B 18/00* | (2006.01) | |
| *A61B 90/00* | (2016.01) | |

(52) U.S. Cl.
CPC .............. *A61B 2017/00084* (2013.01); *A61B 2018/00011* (2013.01); *A61B 2018/00017* (2013.01); *A61B 2018/0022* (2013.01); *A61B 2018/00023* (2013.01); *A61B 2018/00214* (2013.01); *A61B 2018/00226* (2013.01); *A61B 2018/00351* (2013.01); *A61B 2018/00363* (2013.01); *A61B 2018/00577* (2013.01); *A61B 2018/00714* (2013.01); *A61B 2018/00791* (2013.01); *A61B 2018/00839* (2013.01); *A61B 2018/00863* (2013.01); *A61B 2018/00875* (2013.01); *A61B 2018/00892* (2013.01); *A61B 2018/0212* (2013.01); *A61B 2018/0262* (2013.01); *A61B 2090/064* (2016.02); *A61B 2090/065* (2016.02)

(58) Field of Classification Search
CPC ...... A61B 18/1492; A61B 2017/00084; A61B 2018/00363; A61B 2018/00791; A61B 2018/00839; A61B 2018/00875; A61B 2018/00892; A61B 2090/064; A61B 2090/065; A61B 18/02–0218; A61B 2018/0212–0293; A61F 7/00–123; A61F 2007/0001–126
See application file for complete search history.

(56) References Cited

U.S. PATENT DOCUMENTS

| | | |
|---|---|---|
| 5,437,673 A | 8/1995 | Baust et al. |
| 5,674,218 A | 10/1997 | Rubinsky et al. |
| 5,758,505 A | 6/1998 | Dobak et al. |
| 5,759,182 A | 6/1998 | Varney et al. |
| 5,833,685 A | 11/1998 | Tortal et al. |
| 5,871,526 A * | 2/1999 | Gibbs ...................... A61F 7/02 607/104 |
| 5,885,276 A | 3/1999 | Ammar et al. |
| 5,901,783 A | 5/1999 | Dobak et al. |
| 6,014,864 A | 1/2000 | Owen |
| 6,035,657 A | 3/2000 | Dobak et al. |
| 6,471,694 B1 | 10/2002 | Kudaravalli et al. |
| 6,505,629 B1 | 1/2003 | Mikus et al. |
| 6,508,814 B2 | 1/2003 | Tortal et al. |
| 6,530,234 B1 | 3/2003 | Dobak et al. |
| 6,547,785 B1 | 4/2003 | Heiner et al. |
| 6,565,556 B1 | 5/2003 | Korpan et al. |
| 6,592,577 B2 | 7/2003 | Abboud et al. |
| 6,858,025 B2 | 2/2005 | Maurice |
| 7,083,612 B2 | 8/2006 | Littrup et al. |
| 7,160,290 B2 | 1/2007 | Eberl et al. |
| 7,179,254 B2 | 2/2007 | Pendekanti et al. |
| 7,181,927 B2 | 2/2007 | Collins et al. |
| 7,192,426 B2 | 3/2007 | Baust et al. |
| 7,237,555 B2 | 7/2007 | Kochamba et al. |
| 7,291,142 B2 | 11/2007 | Eberl et al. |
| 7,367,341 B2 | 5/2008 | Anderson et al. |
| 7,416,548 B2 | 8/2008 | Baust et al. |
| 7,594,915 B2 | 9/2009 | Kochamba et al. |
| 7,846,154 B2 | 12/2010 | Bliweis et al. |
| 7,909,227 B2 * | 3/2011 | Duong ................... A61B 18/02 228/44.5 |
| 7,972,327 B2 | 7/2011 | Eberl et al. |
| 8,235,977 B2 | 8/2012 | Bencini |
| 8,439,905 B2 | 5/2013 | Baust et al. |
| 8,465,481 B2 | 6/2013 | Mazzone et al. |
| 8,551,081 B2 | 10/2013 | Baust et al. |
| 8,579,889 B2 | 11/2013 | Bencini |
| 8,632,529 B2 | 1/2014 | Bencini |
| 8,784,409 B2 | 7/2014 | Robilotto et al. |
| 8,814,850 B2 | 8/2014 | Babkin et al. |
| 8,945,106 B2 | 2/2015 | Arless et al. |
| 8,998,888 B2 | 4/2015 | Baust et al. |
| 9,033,965 B2 | 5/2015 | Ingle et al. |
| 9,078,733 B2 | 7/2015 | Ramadhyani et al. |
| 9,089,314 B2 | 7/2015 | Wittenberger |
| 9,089,316 B2 | 7/2015 | Baust et al. |
| 9,131,836 B2 | 9/2015 | Huszar et al. |
| 9,308,120 B2 | 4/2016 | Anderson et al. |
| 9,314,368 B2 | 4/2016 | Allison et al. |
| 9,345,527 B2 | 5/2016 | Babkin et al. |
| 9,408,654 B2 | 8/2016 | Baust et al. |
| 9,414,738 B2 | 8/2016 | Huszar et al. |
| 9,532,703 B2 | 1/2017 | Huszar et al. |
| 2001/0021847 A1 | 9/2001 | Abboud et al. |
| 2003/0060685 A1 | 3/2003 | Houser et al. |
| 2003/0125721 A1 | 7/2003 | Yon et al. |
| 2003/0153905 A1 | 8/2003 | Edwards et al. |
| 2004/0006379 A1 | 1/2004 | Brett |
| 2004/0122500 A1 | 6/2004 | Rouns |
| 2005/0159735 A1 | 7/2005 | Walton et al. |
| 2006/0210605 A1 | 9/2006 | Chang et al. |
| 2007/0185477 A1 | 8/2007 | Hooven |
| 2007/0233055 A1 | 10/2007 | Abboud et al. |
| 2007/0233226 A1 | 10/2007 | Kochamba et al. |
| 2007/0277550 A1 | 12/2007 | Li et al. |
| 2007/0287994 A1 | 12/2007 | Patel |
| 2008/0077126 A1 | 3/2008 | Rashidi |
| 2009/0043297 A1 | 2/2009 | Baust et al. |
| 2009/0088735 A1 | 4/2009 | Abboud et al. |
| 2009/0182317 A1 | 7/2009 | Bencini |
| 2009/0326511 A1 | 12/2009 | Shivkumar |
| 2010/0057064 A1 | 3/2010 | Baust et al. |
| 2011/0034912 A1 | 2/2011 | de Graff et al. |
| 2011/0282203 A1 | 11/2011 | Tsoref et al. |
| 2012/0041526 A1 * | 2/2012 | Stormby .................. A61F 7/10 607/104 |
| 2012/0089047 A1 | 4/2012 | Ryba et al. |
| 2012/0143131 A1 | 6/2012 | Tun et al. |
| 2012/0288848 A1 * | 11/2012 | Latham ..................... A61F 7/02 435/1.1 |
| 2014/0236271 A1 * | 8/2014 | Fronda ..................... A61F 7/10 607/104 |
| 2014/0303696 A1 | 10/2014 | Anderson et al. |
| 2014/0303697 A1 | 10/2014 | Anderson et al. |
| 2014/0336636 A1 | 11/2014 | Huszar et al. |
| 2014/0350537 A1 | 11/2014 | Baust et al. |
| 2014/0371733 A1 | 12/2014 | Nydam et al. |
| 2015/0018810 A1 | 1/2015 | Baust et al. |
| 2015/0257810 A1 | 9/2015 | Baust et al. |
| 2015/0300569 A1 | 10/2015 | Baust et al. |
| 2016/0001018 A1 | 1/2016 | Fink et al. |
| 2016/0022345 A1 | 1/2016 | Baust et al. |
| 2016/0298888 A1 | 10/2016 | Khatri et al. |
| 2016/0338752 A1 | 11/2016 | Sperling |
| 2016/0338754 A1 | 11/2016 | Baust et al. |
| 2017/0000543 A1 | 1/2017 | Mahrouche et al. |
| 2017/0000544 A1 | 1/2017 | Mahrouche et al. |

FOREIGN PATENT DOCUMENTS

| | | |
|---|---|---|
| EP | 3120792 A1 | 1/2017 |
| JP | 06315497 A | 11/1994 |
| JP | H06315497 A | 11/1994 |
| JP | 2017500928 A | 1/2017 |
| WO | WO-2015081019 A2 * | 6/2015 ............. A61B 90/04 |

* cited by examiner

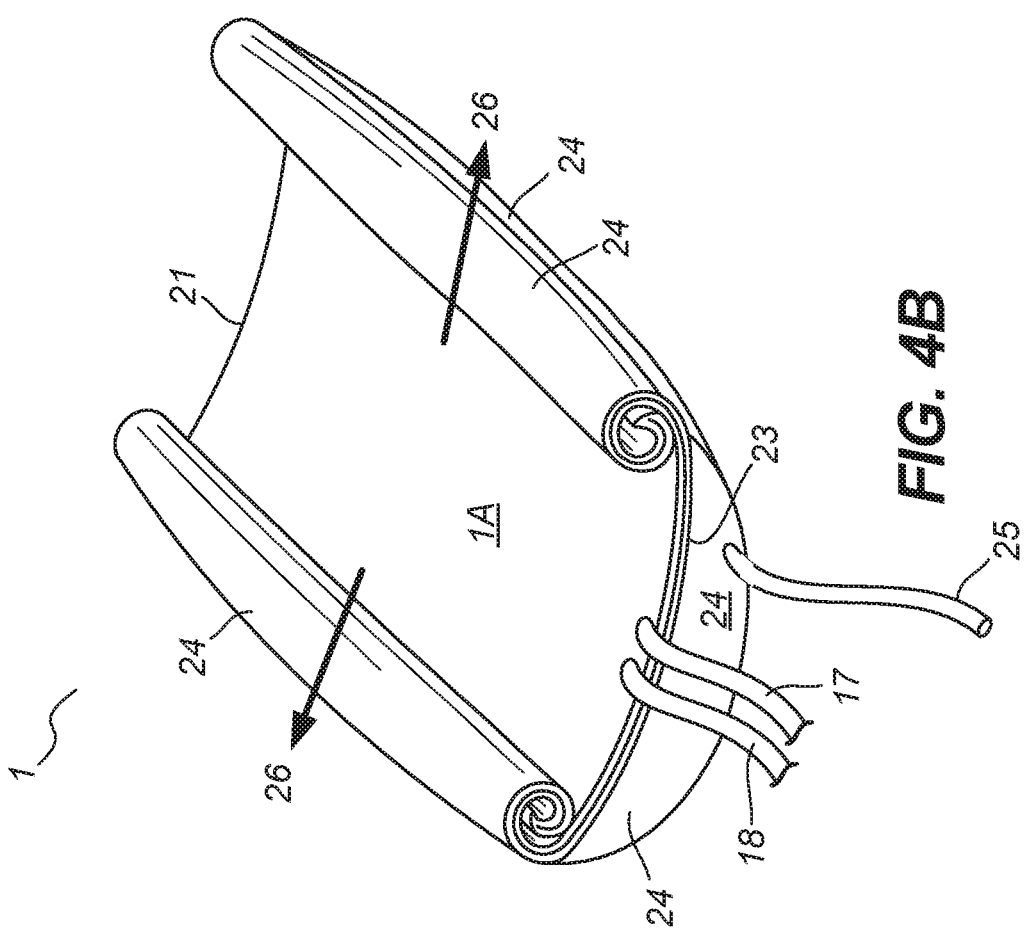
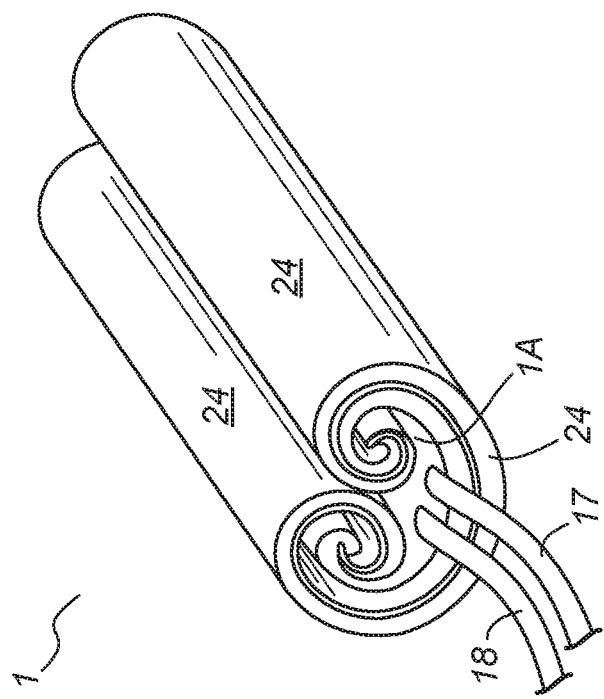

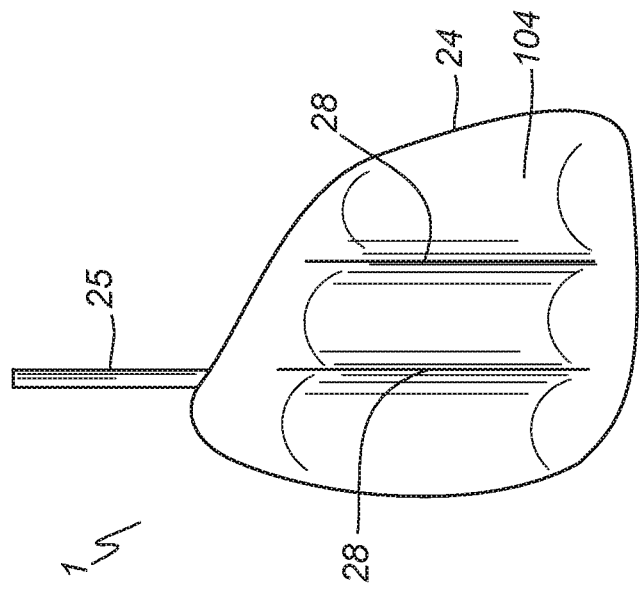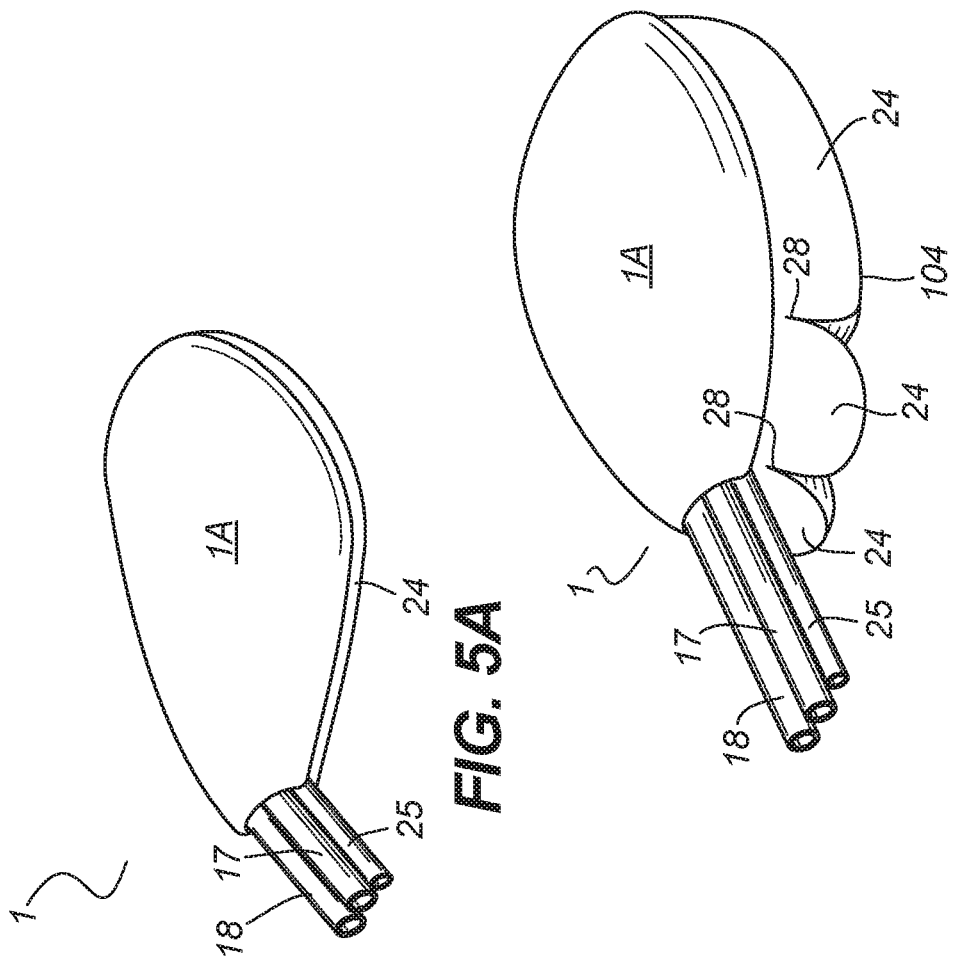

DEVICE FOR ABLATION OF TISSUE SURFACES AND RELATED SYSTEMS AND METHODS

CROSS-REFERENCE TO RELATED APPLICATION(S)

This application claims the benefit under 35 U.S.C. § 119(e) to U.S. Provisional Application 62/446,976, filed Jan. 17, 2017 and entitled "Device for Ablation of Flat Tissue Surfaces and Related Systems and Methods;" U.S. Provisional Application 62/461,930, filed Feb. 22, 2017 and entitled "Device for Ablation of Flat Tissue Surfaces and Related Systems and Methods;" and U.S. Provisional Application 62/596,239, filed Dec. 8, 2017 and entitled "Device for Ablation of Flat Tissue Surfaces and Related Systems and Methods;" all of which are hereby incorporated herein by reference in their entireties.

FIELD OF THE INVENTION

The various embodiments herein relate to ablation devices, and more specifically to an ablation device that can ablate tissue surfaces such as large and/or substantially flat tissue surfaces, including, for example, an external wall of a patient's heart, while insulating or protecting adjacent tissues from ablation.

BACKGROUND OF THE INVENTION

Cardiac rhythm disorders often originate within the left atrium heart chamber, and more so when the left atrium develops hypertension and enlarges, which is common in Western societies either as a general consequence of aging or as a secondary effect of other conditions, including valvular heart disease, essential hypertension, sleep apnea, and others. A common left atrial rhythm disorder called atrial fibrillation is often caused by aberrant electricity generated within the junctions of the pulmonary veins and the left atrium heart chamber. Chronic atrial fibrillation is associated with premature mortality, stroke, heart failure, dementia and symptoms of low energy and exercise intolerance. It is a health scourge that robs people of their quality of life and substantially increases the cost the health care worldwide.

Electrical activity in these locations can be ablated relatively easily using percutaneous catheter-based tools, with a reliable degree of success in earlier-stage atrial fibrillation scenarios. For example, in some known devices, the delivery chamber is typically a linear metal cryoprobe, which becomes pressurized with the cold gas and is used for intravenous or internal (internal to an organ) ablation by being held against the target tissue for a sufficient duration to cause tissue ablation. Other known devices have a delivery chamber that consists of a balloon within a balloon comprised of medical grade plastic that can withstand very high pressures. When pressurized, this two-layer device assumes a spherical configuration for internal ablation of tubular structures like large (pulmonary) veins via an intravenous approach.

Unfortunately, the majority of atrial fibrillation cases seen in clinical practice are advanced stage, and aberrant electricity is located not only within the pulmonary vein-left atrial junctions, but also in the large area of atrial tissue between the veins that comprises the 'back' or 'posterior' wall of the left atrium heart chamber. As this part of the left atrium enlarges over time, the combination of increased mass of electrically conductive tissue and scattered scar formation set up a condition called persistent or chronic atrial fibrillation, which has eluded successful treatment with percutaneous catheter ablation. In addition, the "free" wall of the right atrium can also be a source of aberrant electrical activity in very advanced cases of chronic atrial fibrillation. The reason catheter treatment fails for this condition is actually rather simple: each of the posterior left atrium and the "free" wall of the right atrium comprises a large surface area (similar to that of a human palm) that is simply too tedious and difficult to ablate sufficiently well with small catheter-based tools.

Several problems exist attempting to ablate large surface areas of tissue in general. For example, intravenous catheters and expandable devices positioned inside the heart must ablate larger areas of tissue in a piecemeal fashion and generally without direct visualization of the target tissue, which creates an inherent risk that important tissue gaps may be left untreated, thereby potentially leading to failures. Further, when attempting to ablate larger areas of tissue from the outside of the heart ('epicardial' locations), two major problems exist. The first is that whether using heat or cold energy for ablation, the flowing blood in the heart chamber is constantly working to counteract ablation of the target tissue from its opposite side. For instance, since blood flows within the left atrium heart chamber at a rate of around 5 liters/minute at 37 degrees Celsius ("C"), external ablation sources that destroy tissue by heating them (i.e. radiofrequency, laser) are less effective because of the constant flow of 37° C. blood. That is, the steady flow of blood effectively "cools"—by both convection and conduction—the tissue being heated, such that the cooling effect is difficult to overcome. Similarly, attempts to ablate a large area of atrial tissue by freezing (cryoablation) will also be impeded by the 37° C. flowing blood that warms the very same tissue being cooled. The second major problem with ablation of a large area of tissue from outside the heart is that the extreme temperature (either hot or cold) of the ablation device can inadvertently heat or cool adjacent, non-target tissues, thereby causing unintended damage.

Another important heart rhythm disturbance that begs a better solution is ventricular tachycardia, which is an electrical problem originating within a smaller area of tissue (as compared with atrial fibrillation), but also a much thicker area and density of tissue that is also very challenging to ablate using standard catheter-based techniques. These smaller segments of ventricular muscle are actively warmed not only by flowing blood in the ventricular heart chamber, but by a rich network of blood vessels large and small that course through the muscle to nourish it and also keep it warm.

There is a need in the art for improved methods, systems, and devices for ablating a tissue surface, including, for example, a large, substantially flat tissue surface, such as an exterior wall of a patient's heart.

BRIEF SUMMARY OF THE INVENTION

Discussed herein are various ablation systems and ablation components for use with such systems.

In Example 1, a system for ablating a generally planar surface of tissue that comprises an ablation component comprising a first chamber defined in the ablation component and an inflatable second chamber defined in the ablation component, wherein the second chamber is a low thermal conductivity chamber. The first chamber comprises a plurality of channels defined along an external wall in the first chamber, wherein the plurality of channels define a fluid pathway within the first chamber, an intake port operably coupled to the first chamber, wherein the intake port is in fluid communication with the plurality of channels, and an outlet port operably coupled to the first chamber, wherein the outlet port is in fluid communication with the plurality of channels, wherein the external wall of the first chamber is substantially flat.

Example 2 relates to the system according to Example 1, wherein the plurality of channels are constructed and arranged to receive a continuous flow of a fluid that is sufficiently cold or hot to ablate target tissue adjacent to the first chamber via thermal conductance.

Example 3 relates to the system according to Example 2, wherein the fluid is helium gas that is sufficiently cold to ablate the target tissue.

Example 4 relates to the system according to Example 1, wherein the second chamber is configured to be capable of insulating tissue adjacent to the target tissue during an ablation procedure.

Example 5 relates to the system according to Example 1, wherein the plurality of channels are defined by channel walls in the first chamber.

Example 6 relates to the system according to Example 1, wherein the plurality of channels form a maze-like pattern in the first chamber.

Example 7 relates to the system according to Example 1, wherein the first chamber first comprises at least one baffle wall defined within at least one of the plurality of channels.

Example 8 relates to the system according to Example 1, wherein the fluid pathway is a substantially unidirectional pathway defined from the intake port to the outlet port.

Example 9 relates to the system according to Example 1, wherein the a length of the fluid pathway is greater than a length or width of the first chamber.

Example 10 relates to the system according to Example 1, further comprising a fluid source and a cooler, wherein the cooler is disposed downstream of the fluid source and upstream of the ablation component.

Example 11 relates to the system according to Example 10, further comprising a pre-cooler disposed upstream of the cooler, wherein the pre-cooler is a recuperator.

Example 12 relates to the system according to Example 1, wherein the ablation component comprises a collapsed configuration and a deployed configuration.

Example 13 relates to the system according to Example 1, wherein said second chamber comprises a generally compliant inflatable cushion.

Example 14 relates to the system according to Example 13, wherein the second chamber comprises at least one baffle wall defined therein, wherein the at least one baffle wall is configured to prevent the second chamber from forming a spherical shape when inflated and to cause generally uniform expansion of a height of the cushion along a perimeter thereof.

Example 15 relates to the system according to Example 1, wherein the substantially flat external wall is substantially flat in the absence of contacting any target tissue.

Example 16 relates to the system according to Example 1, wherein the first chamber comprises a plurality of sensors disposed along the external wall.

Example 17 relates to the system according to Example 1, wherein a pressure of a fluid delivered through the intake port has a pressure that is less than or equal to about 40 psi.

Example 18 relates to the system according to Example 1, wherein the second chamber comprises a low thermal conductive design.

Example 19 relates to the system according to Example 1, wherein the second chamber comprises a low thermal conductive material.

Example 20 relates to the system according to Example 1, wherein the plurality of channels are constructed and arranged to receive a continuous flow of a cooling substrate at a predetermined flow rate.

In Example 21, a method for ablating a generally flat surface of tissue comprises positioning an ablation device in a collapsed configuration adjacent to a flat surface of target tissue, actuating the collapsed device into a deployed configuration such that an ablation chamber is in contact with the flat surface of target tissue, cooling a cooling substrate in a cooler such that the cooling substrate is cooled, delivering the cooled cooling substrate into the ablation chamber, ablating the target tissue by advancing the cooled cooling substrate in a continuous flow through a pathway formed in the ablation chamber, whereby the cooled cooling substrate advancing through the pathway creates a substantially uniform temperature along an external wall of the ablation chamber, wherein the cooled cooling substrate becomes warmer as the cooled cooling substrate advances through the pathway, advancing the warmer cooling substrate out of the ablation chamber, and insulating tissues adjacent to the target tissue from ablation with an insulation chamber, wherein the insulation chamber is a low thermal conductivity chamber.

Example 22 relates to the method according to Example 21, further comprising pre-cooling the cooling substrate in a pre-cooler such that the cooling substrate is pre-cooled prior to cooling the cooling substrate.

Example 23 relates to the method according to Example 22, wherein the pre-cooler is a recuperator, wherein the pre-cooling the cooling substrate further comprises advancing the warmer cooling substrate from the ablation chamber to the recuperator such that the warmer cooling substrate is used to pre-cool the cooling substrate prior to cooling the cooling substrate.

Example 24 relates to the method according to Example 23, further comprising advancing the warmer cooling substrate from the recuperator through the compressor and into the recuperator and pre-cooling the cooling substrate in the recuperator.

Example 25 relates to the method according to Example 23, further comprising advancing the pre-cooled cooling substrate toward the cooler and repeating the cooling, delivering, and ablating steps.

Example 26 relates to the method according to Example 21, wherein the cooling substrate is helium gas.

Example 27 relates to the method according to Example 21, further comprising subsequently warming the ablation chamber by advancing a warming substrate through the pathway formed in the ablation chamber.

Example 28 relates to the method according to Example 26, further comprising first warming the warming substrate in a warmer prior to advancing the warming substrate through the pathway formed in the ablation chamber.

In Example 29, a closed-loop system for ablating a tissue surface comprises a substrate source comprising a cooling substrate, wherein the cooling substrate is helium, a pre-cooler disposed downstream of the substrate source, a cooler disposed downstream of the pre-cooler, an ablation component disposed downstream of the cooler, and a compressor disposed downstream of the pre-cooler and upstream of the pre-cooler. The ablation component comprises an ablation chamber defined in the ablation component and an inflatable insulation chamber defined in the ablation component. The ablation chamber comprises an intake port in fluidic communication with the cooler, at least one channel defined in the first chamber and in fluidic communication with the intake port, wherein the at least one channel defines a unidirectional fluid pathway within the ablation chamber, and an outlet port in fluidic communication with the at least one channel, wherein the outlet port is in fluidic communication with the pre-cooler such that the pre-cooler is downstream of the outlet port.

Example 30 relates to the closed-loop system according to Example 29, wherein an external wall of the ablation chamber is substantially flat.

Example 31 relates to the closed-loop system according to Example 29, wherein the cooler comprises a cooler chamber comprising liquid nitrogen, and a conduit disposed within the cooler chamber, wherein the conduit is in fluid communication with the pre-cooler and the intake port, wherein the conduit comprises a coiled length.

Example 32 relates to the closed-loop system according to Example 31, further comprising a coolant container in fluid communication with the cooler chamber, wherein the coolant container is configured to deliver liquid nitrogen to the cooler chamber such that the conduit is disposable within the liquid nitrogen.

Example 33 relates to the closed-loop system according to Example 29, wherein the compressor is constructed and arranged to continually urge helium to pass through the fluid pathway in a continuous flow at a predetermined rate.

Example 34 relates to the closed-loop system according to Example 29, wherein the fluid pathway comprises a length that is greater than a perimeter of the ablation chamber.

Example 35 relates to the closed-loop system according to Example 29, wherein the insulation chamber comprises a generally compliant inflatable cushion, wherein the inflatable cushion is inflatable with argon gas.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 4A shows a device in a collapsed or folded state, according to one embodiment.

FIG. 4B depicts the device of FIG. 4A being unfolded as the insulation chamber is partially inflated.

FIG. 5A shows a perspective view of a pad with an uninflated insulation chamber, according to one embodiment.

FIG. 5B depicts a perspective view of the pad of FIG. 5A with the insulation chamber inflated, according to one embodiment.

FIG. 5C depicts a perspective view of the underside or insulation chamber side of the pad of FIG. 5A, depicting welded or bonded baffles that prevent the chamber from assuming a spherical shape, according to one embodiment.

DETAILED DESCRIPTION

Discussed herein are various ablation devices and related systems and methods for ablating tissue surfaces, including, for example, large and/or generally flat tissue surfaces. Certain embodiments relate to systems and devices that can ablate the entirety or majority of an exterior wall of a patient's heart (including for example, an exposed segment of the posterior wall of the left atrium or the free wall of the right atrium) safely, quickly and effectively. Further, in certain implementations, the devices utilize cryoablation. Further, according to certain embodiments, the target tissue surfaces are being actively and naturally warmed by a significant heat sink in the form of internal flowing blood, and the various ablation devices herein are configured to overcome that heat sink.

Figure 1:
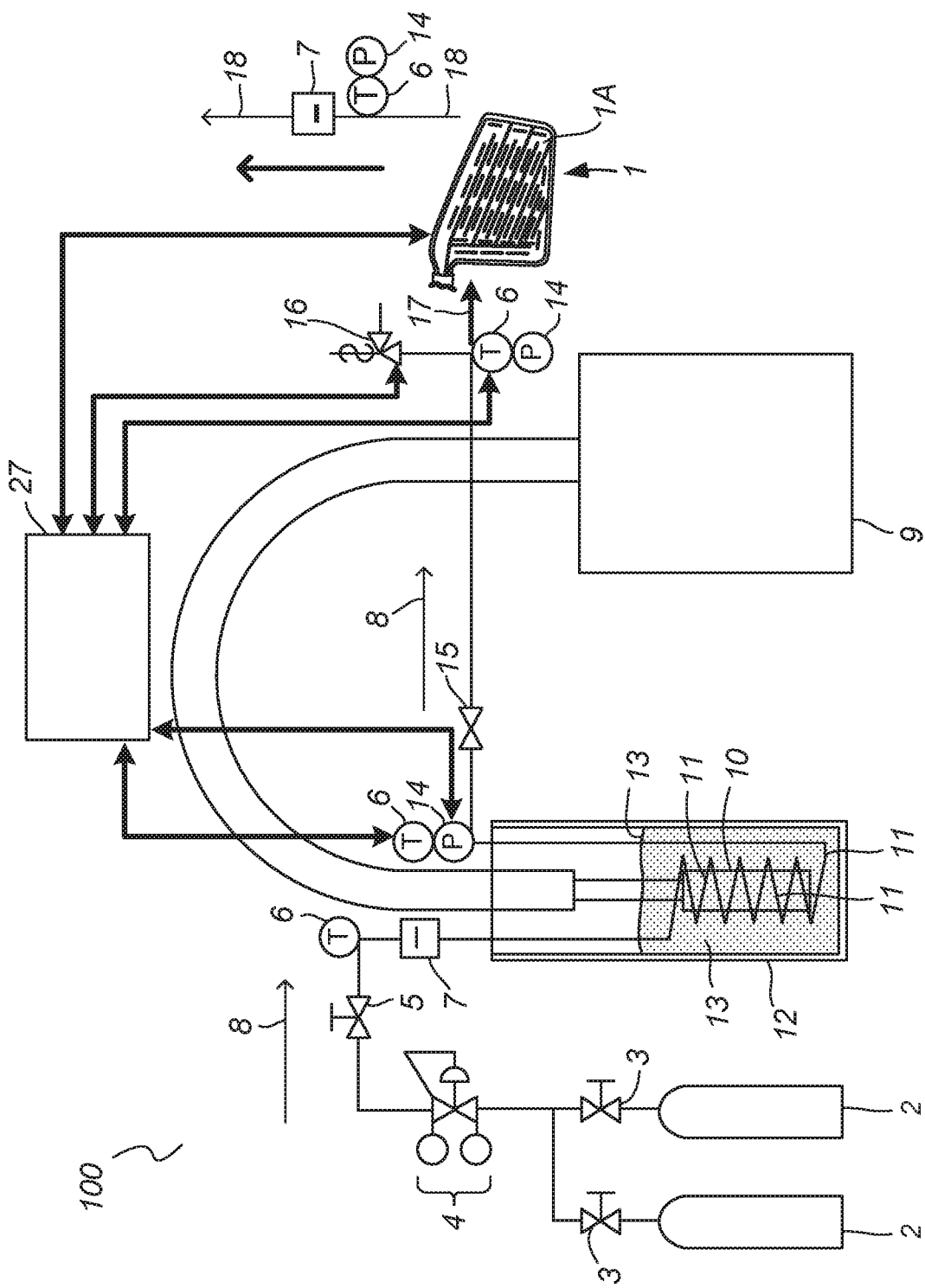
FIG. 1 is a schematic view of an ablation system, according to one embodiment.

Certain embodiments as described in further detail herein are cryoablation systems and/or devices that have a freezing mechanism for ablation of the target tissue. Such systems have extremely cold gas that is passed into an ablation structure that then contacts living tissue such that heat is extracted from the tissue and ice forms inside the tissue's cells, which causes cell death. In one specific exemplary embodiment as shown in FIG. 1, a cryoablation system 100 has an ablation and insulation pad 1 (referred to herein as simply "ablation pad" or "pad"), such that the system 100 delivers coolant (also referred to as "cooling substrate") in the form of ultra-cold gas to the pad 1 for ablation of target tissue. The system 100 as shown has two pressurized cylinders of gas 2 that provide the cooling substrate. In one embodiment, the coolant gas is argon, nitric oxide, or helium. Further, the gas cylinders 2 can also provide a warming substrate in the form of a different gas to be supplied to the pad 1 after application of the cold gas, as will be described in additional detail below. For example, the warming substrate can be helium. Alternatively, the system 100 can have only one cylinder 2. In a further alternative, the system 100 can have three or more cylinders. In the system 100, the gas generally flows in the direction indicated by arrows 8.

In one embodiment, standard manifolds with checkvalves 3 are coupled to the cylinders 2 and are used for safety and containment purposes. When opened, the valves 3 allow the coolant to flow through a pressure regulator 4 and then through high-pressure valve 5. According to certain embodiments, a temperature sensor or monitor 6 is disposed downstream from the high pressure valve 5 to monitor the temperature of the coolant flowing therethrough. The cooling substrate is typically around room temperature (around 20 degrees Centigrade) at this point in the system 100.

Continuing with FIG. 1, downstream from the temperature sensor 6 is a flowmeter 7, which gauges the rate of flow of the cooling substrate at this point in the system 100. Typically, according to certain embodiments, the flow rate of the cooling substrate is 1 gram/second at this point in the system 100. From the flowmeter 7, the substrate flows, according to one embodiment, into a substrate cooler (also referred to as a "chiller" or "pre-chiller") 12. In one embodiment, the substrate cooler 12 is an immersion chiller 12. In more specific embodiments, the immersion chiller 12 is a vacuum dewar 12 containing a volume of heat transfer fluid 13, with an immersion probe 10 disposed therein. In one example, the heat transfer fluid 13 is Novec 7000™, which is commercially available from 3M. In this implementation as shown in FIG. 1, the immersion probe 10 is powered by a commercially-available electrically-powered immersion probe cooler 9 that is connected to the probe 10. In one embodiment, the probe cooler 9 is the IP-100 Low Temperature Cooler™, which is available from Polyscience. Alternatively, the probe cooler 9 can be any known cooler. The cooling substrate flows though tubing 11 that extends into the chiller 12 and is coiled around the immersion probe 10. The positioning of the tubing 11 around the probe 10 results in the probe 10 causing the temperature of the coolant gas in the tubing 11 to drop, thereby resulting in the substantial cooling of the cooling substrate. In one implementation, the probe 10 reaches a temperature of −100° C. Alternatively, any known gas cooling or chilling device can be used as the substrate cooler 12.

Downstream of the coiled configuration, the tubing 11 extends out of the immersion chiller 12. In certain implementations, a temperature sensor 6 is disposed along the tubing 11 downstream of the chiller 12 to monitor the temperature drop of the coolant gas as a result of flowing through the chiller 12. In one embodiment, the temperature of the cooling substrate is around negative 63 degrees Centigrade after passing through the gas cooler 12. According to some implementations, a pressure gauge 14 is also disposed along the tubing 11 downstream of the chiller 12. The cooling substrate is expected to have a pressure of around 100 atm, according to one embodiment.

Downstream of the pre-chiller 12 (and any optional temperature sensor 6 and/or pressure gauge 14) is the restrictor array 15. According to certain embodiments as discussed elsewhere herein, the restrictor array 15 is a Joule-Thomson restrictor array 15 that utilizes the Joule-Thomson effect to further cool the cooling substrate while also lowering the pressure thereof. In one implementation, as the coolant gas exits the array 15, the gas has a substantially lower pressure and a substantially lower temperature than the coolant gas had as it entered the array 15. According to certain embodiments, the cooling substrate exiting the array 15 has a pressure of around 1.5 atm and a temperature of around −140° C.

Figure 6:
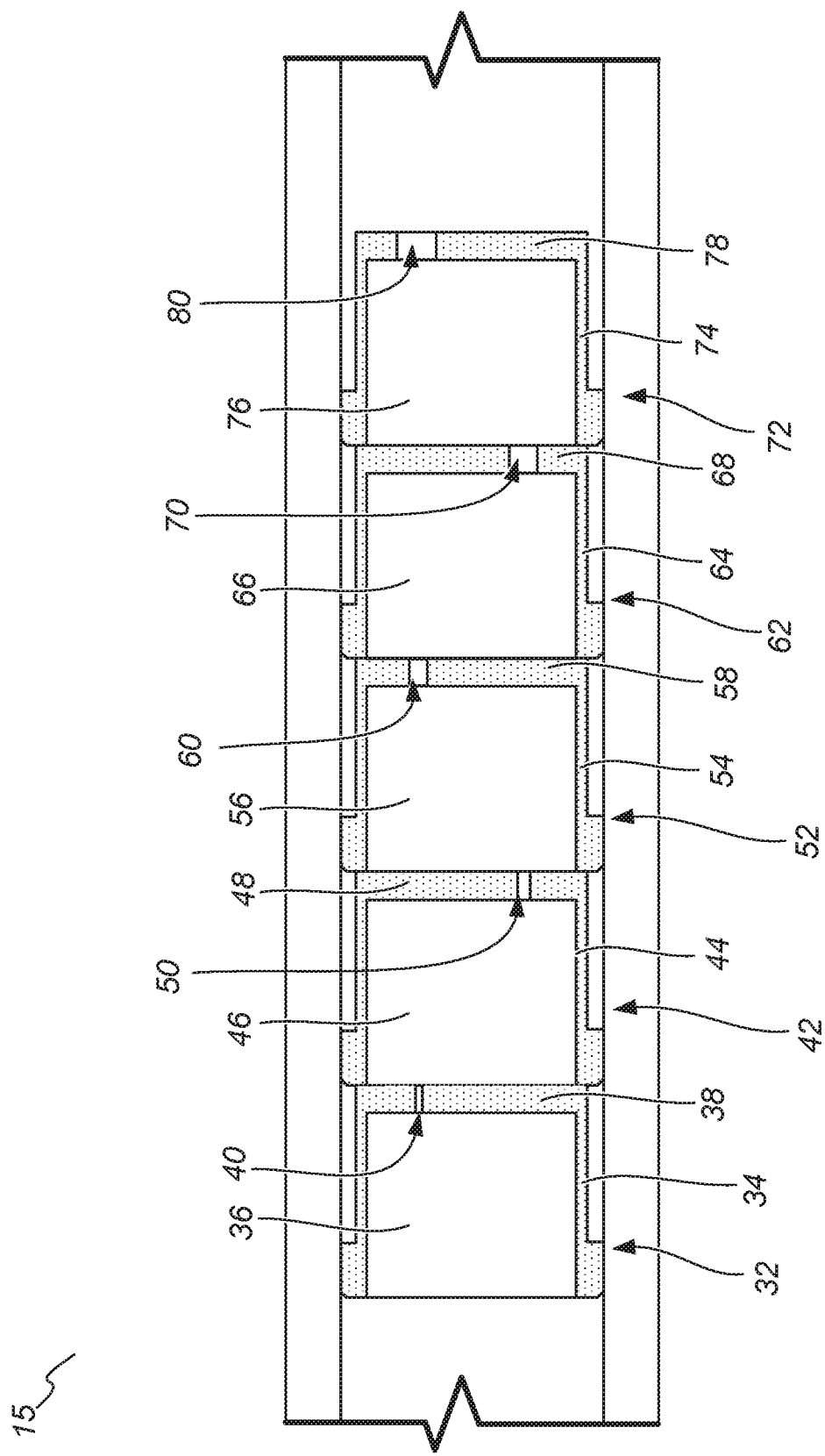
FIG. 6 is a side, cross-sectional view of a restrictor array, according to one embodiment.

In one specific embodiment as depicted in FIG. 6, the restrictor array 15 is a small (also referred to herein as "miniaturized") array of five restrictors 32, 42, 52, 62, 72. Each of the restrictors 32, 42, 52, 62, 72 has a restrictor body 34, 44, 54, 64, 74 that defines a chamber 36, 46, 56, 66, 76. Each of the restrictor bodies 34, 44, 54, 64, 74 has an external diameter that is slightly smaller than the internal diameter of the tubular line in the system 100. The distal end of each body 34, 44, 54, 64, 74 has a distal wall 38, 48, 58, 68, 78 with a small opening 40, 50, 60, 70, 80 defined therein that is in fluid communication with the chamber 36, 46, 56, 66, 76. The array 15 is structured so that the cooling substrate passes through each of the restrictors 32 42, 52, 62, 72 in succession, thereby passing through the entire array 15. In one embodiment, each of the openings 40, 50, 60, 70, 80 has a successively larger diameter than each opening proximal thereto. In other words, in this specific implementation, the opening 50 in the restrictor 42 has a larger diameter than the opening 40 in restrictor 32. Further, the opening 60 in restrictor 52 has a larger diameter than the opening 40, the opening 70 has a larger diameter than the opening 60, and the opening 80 has a larger diameter than the opening 70.

According to one specific embodiment, the axial length of each of the restrictor bodies 34, 44, 54, 64, 74 is less than 0.25 inches, and the total axial length of the restrictor with all five bodies coupled as shown is about 1 inch. Further, the outer diameter of each body 34, 44, 54, 64, 74 is around 0.25 inches. In this embodiment, the opening 40 in body 34 has a diameter of about 0.007 inches, the opening 50 has a diameter of about 0.011 inches, the opening 60 has a diameter of about 0.017 inches, the opening 70 has a diameter of about 0.025 inches, and the opening 80 has a diameter of about 0.037 inches. In this embodiment, if the gas is pre-chilled and delivered to the array 15 with a temperature of 210 Kelvin and a pressure of 100 atm, the gas will drop to a temperature of 176 K and a pressure of 42 atm when it passes through the opening 40 and into the chamber 46. Further, when the gas passes through opening 50, it will drop to a temperature of 155 K and a pressure of 18 atm. And when the gas passes through the opening 60, it will drop to a temperature of 143 K and an atmosphere of 8 atm. In addition, when the gas passes through the opening 70, the temperature will drop to 136 K and a pressure of 3.6 atm. Finally, when the gas passes through the opening 80, the temperature will drop to 134 K and a pressure of 1.5 atm.

In alternative embodiments, the restrictor array 15 can constitute any number of restrictors ranging from one restrictor to ten restrictors or more. For example, the array 15 can be made up of one, two, three, or four restrictors. Alternatively, the array 15 can be made up of more than five restrictors. Further, the restrictors in the array 15 can have any known restrictor characteristics and/or dimensions, so long as the array 15 causes the cooling substrate to exit the array 15 at a lower temperature and a lower pressure than entering the array 15.

Returning to FIG. 1, in certain implementations, a temperature sensor 6 is disposed downstream of the array 15 to monitor the temperature drop of the cooling substrate as a result of flowing through the array 15, and a pressure gauge 14 can also be disposed downstream of the array 15 to monitor the pressure drop. In addition, according to certain alternative embodiments, a pressure-relief valve 16 may also be incorporated into the system 100 at this or another downstream position as a safety mechanism to avoid over-pressurization of the ablation pad 1. In other words, in the event that the gas pressure does not get lowered to the target pressure as a result of passage through the restrictor array 15, the pressure-relief valve 16 can ensure that the pressure is lowered to an acceptable pressure prior to entering the pad 1. For example, in one embodiment, the pressure-relief valve 16 ensures that the pressure does not exceed 1.5 atm. Alternatively, the pressure-relief valve 16 can be used to ensure that the pressure does not exceed any predetermined pressure.

According to certain embodiments, the pressure of the gas delivered to any ablation pad in any system disclosed or contemplated herein is low. For example, the pressure of the gas delivered to any ablation pad herein, in certain implementations, does not exceed around 1.5 atmospheres as it enters the pad. Put another way, in certain embodiments, the pressure of the cooling substrate as it enters the ablation chamber is about 15 pounds per square inch ("psi") or less. Alternatively, the pressure of the cooling substrate can be around 40 psi or less as it enters the pad. In these implementations, it can preferable to keep the gas pressure within the ablation chamber or body as low as possible. Gas pressure that is too high could risk rupture of the ablation chamber and spilling of cold gas directly into contact with human tissues. Alternatively, the various pad embodiments herein can be constructed to withstand higher pressures.

According to one embodiment, this system 100 (and any other system embodiment disclosed or contemplated herein) is a closed-loop system 100 in which the cooling substrate exiting the ablation pad 1 via the output line 18 is retained within the system 100 and cycled back through using a compressor (not shown). This closed-loop configuration conserves the cooling substrate through re-use, rather than simply venting the cooling substrate and requiring 100% of the additional cooling substrate be new substrate that hasn't already passed through the system 100.

According to one embodiment, the ultra-cold gas flows into the ablation chamber 1A of the ablation device 1 via a dedicated inlet line 17. It is understood that the ablation pad 1 can be any known ablation pad or device that can be coupled to the system 100. In certain implementations discussed below in additional detail and depicted in FIGS. 2A and 2B, along with other embodiments as discussed and depicted elsewhere herein, the pad 1 can have a multitude of channels in the ablation chamber 1A through which the cooling substrate can flow. The gas then exits the chamber 1A via a dedicated outlet or exhaust line 18. In certain embodiments, a temperature sensor 6 is disposed downstream of the pad 1 to monitor the temperature of the gas after flowing through the chamber 1A, and a pressure gauge 14 can also be disposed downstream of the pad 1 to monitor the pressure. In accordance with various implementations, it is expected that the pressure will be lower after passing through the pad 1, with a pressure of around 1 atm according to certain embodiments. Further, it is expected that the temperature of the gas has risen as a result of absorbing energy from the target tissue during ablation, with the temperature being around −60 degrees Centigrade in certain examples. A flowmeter 7 can also be disposed downstream of the pad 1 according to certain embodiments. The flowmeter measures the flow rate of the gas exiting the chamber 1A. In certain implementations, it is expected that the flow rate is substantially unchanged at around 1 gram/second. In one embodiment, the flowmeter 7 can be used to confirm that no leakage of gas has occurred during passage of the gas through the system between the first flowmeter 7 upstream of the chiller 12 and the flowmeter 7 downstream of the pad 1.

In accordance with certain implementations, the cooling of the cooling substrate in a chiller 12 upstream of the restrictor array 15 (essentially pre-chilling the gas) provides the advantage of producing the desired ultra-low temperature cooling substrate at a substantially lower pressure compared with the higher atmospheric pressures associated with known closed-system cryoprobes or balloons as the gas is delivered into the ablation chamber 1A. That is, supplying pre-cooled gas to a Joule-Thomson restrictor array 15 allows for the gas to achieve target temperatures at a lower pressure than if the gas were not pre-cooled. Thus, the gas exiting the array 15 and entering the chamber 1A can achieve the target cold temperature at a lower pressure than if the system 100 did not have a substrate cooler 12 upstream of the restrictor array 15. In various embodiments, the lower pressure (less than 2 atm, for example, in certain embodiments) allows for the chamber 1A to be constructed of a plastic material or other pliable material that can maintain or be deployed into a desired shape, such as a substantially flat shape, as engineered without risk of breaches or deformation to unwanted spherical configurations.

When the ablation procedure is complete, in certain embodiments, a different cylinder 2 can be coupled to the system 100 that provides a different gas (such as, in certain exemplary embodiments, helium gas) as a warming substrate. The system 100 can be reconfigured such that the warming substrate bypasses the chiller 12 and instead goes directly to and passes through the Joule-Thomson restrictor 15. In this embodiment, the gas that is passed through the array 15 is warmed by the array 15 (rather than cooled). The warmed gas is then delivered to the ablation chamber 1A, facilitating both ablation injury by freeze-thaw cycle and removal of the pad 1 from the patient. Alternatively, in those embodiments in which the system 100 (or any system herein) is a closed-loop system, the system 100 includes a valve that diverts the cooling substrate away from the cooling cycle described above. The diverted substrate is then passed through a warmer that warms the substrate to 37° C. (such that it becomes a warming substrate) and caused to flow through the ablation chamber 1A to thaw the pad 1 and cause it to release from the target tissue.

Figures 3A, 3B:
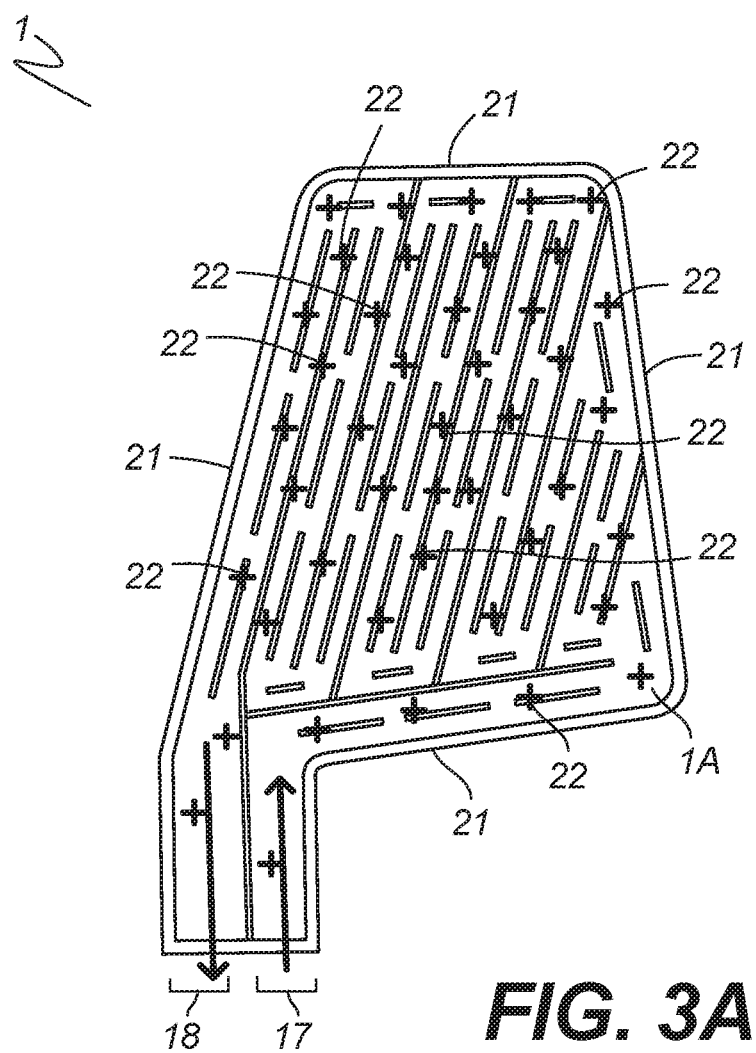
FIG. 3A is another aerial view of the ablating surface of the pad showing a multitude of sensors on its surface, according to one embodiment.
FIG. 3B depicts a graphic user interface that displays monitoring information (temperature, voltage), safety controls and system controls, according to one embodiment.

In accordance with one implementation, the system 100 can also have a controller 27 that is configured to be communicatively and operationally coupled to the various components of the system 100. That is, the controller 27 is configured to monitor the various components, such as, for example, the chiller 12, the pad 1, and the various sensors 6, 7, 14 and regulators/valves 3, 4, 5, 16. Further, the controller 27 can also be configured to control those components. In one embodiment, the controller 27 has a graphic user interface ("GUI") incorporated therein that can be used by a user to monitor and control the various components of the system 100, including, in some examples, generation and display of voltage maps that can be used to guide therapy and determine if repeat or adjacent area ablation is necessary in larger left atria whose posterior wall surface is larger than the surface of the ablation pad. In one embodiment, the controller 27 can be used to monitor safety and quality aspects of gas delivery, flow, pressure, and temperature as described herein. A controller 27 with a GUI is depicted in FIG. 3B, which is discussed below. In further embodiments, it is understood that the various valves, gauges, and sensors as discussed above and depicted in FIG. 1 are optional.

It is understood that this system 100 embodiment (and any other system embodiment disclosed or contemplated herein) can utilize any known sensors for monitoring any of the various metrics that can be tracked in relation to an ablation system such as these embodiments. For example, in one embodiment, the sensors can include contact force (piezoelectric), voltage, impedance, and temperature sensors. Alternatively, any of the sensors described or contemplated herein can be incorporated into any of the systems herein for their intended uses.

The various ablation pad embodiments disclosed or contemplated herein for use with any of the ablation systems can be shaped with a surface area that is able to contact a target tissue surface, including a large and/or substantially flat tissue surface. It is understood that the term "flat" as used herein in reference to the target tissues is intended to mean any tissue having any substantially or generally flat shape, including slightly rounded tissue or tissue that is not entirely flat. Essentially, the term "flat tissue" is intended to encompass any tissue that is not generally round or spherical. For example, in one specific implementation, the various ablation pads herein can contact most of, or the entire surface of the posterior left atrium in a single application. Each pad embodiment has a body with a first chamber and a second chamber. The first chamber (also referred to as a "first component," "upper chamber," "ablation component," or "ablation chamber") has a generally flat outer surface and is configured to ablate tissue it contacts when actuated by a freezing or heating mechanism. The second chamber (also referred to herein as a "second component," "lower chamber" "insulation component," or "insulation chamber") protects tissues (other than the targeted tissue, such as the posterior left atrial wall) from unintended ablation by insulating those tissues from heating or cooling, generally by interfering with thermal conductance with these tissues by creating distance between them and the upper chamber or body, as well as filling this space or distance with poor thermal conductors such as air, gas, or other polymer material. It is understood that the terms "upper" and "lower" as used herein with respect to the chambers of the pad are not intended to connote specific positions of the chambers or the pad.

Figure 2A:
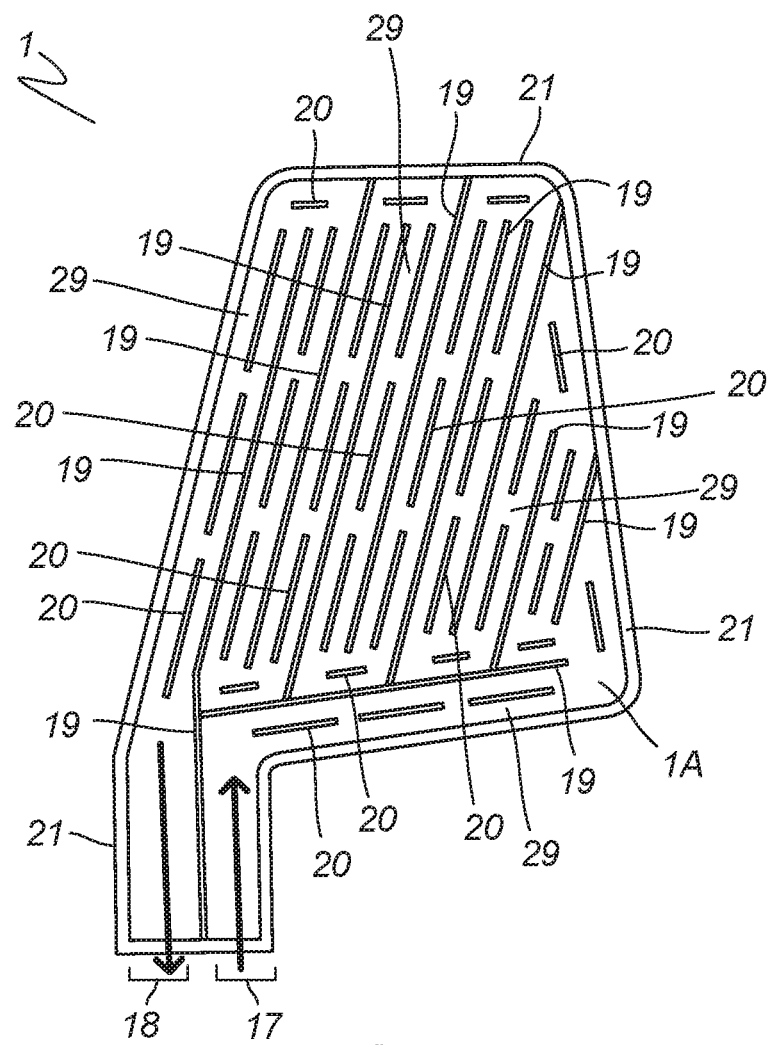
FIG. 2A is top, cross-sectional view of the ablation chamber of an ablation pad, according to one embodiment.
Figure 2B:
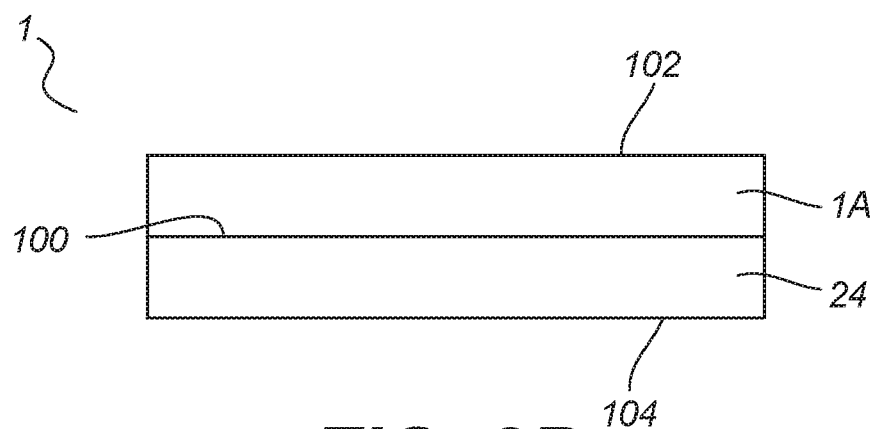
FIG. 2B is a side, cross-sectional view of the ablation pad, according to one embodiment.

According to one embodiment, as shown in FIGS. 2A and 2B, the ablation pad 1 is a substantially flat pad 1 as shown having an ablation chamber 1A and an insulation chamber 24 as described above. The ablation chamber 1A has channels defined therein to ensure flow of gas through the chamber 1A with no or minimal stagnant areas (areas in which the cooling substrate does not flow or has minimal flow) within the chamber 1A. FIG. 2A depicts a top, cross-sectional view of the pad 1—and more specifically, a cross-sectional view of the ablation chamber 1A—that depicts the side of the pad 1 with the ablation chamber 1A visible, while FIG. 2B depicts a side view of the pad 1 that depicts both the ablation chamber 1A and the insulation chamber 24. Dedicated inlet line 17 provides a fluid to the ablation chamber 1A of the pad 1 in the form of cold fluid (such as gas, for example) or warm fluid (such as liquid, for example). Further, the fluidically sealed perimeter 21 of the ablation (upper) chamber 1A of the pad 1 is shown in FIG. 2A.

As best shown in FIG. 2B, the ablation chamber 1A and the insulation chamber 24 are disposed adjacent to each other in the pad 1, thereby resulting in a pad 1 with two chambers or components 1A, 24. In one embodiment, the two chambers 1A, 24 are part of an single, integral pad 1 in which the ablation chamber 1A has an exterior wall (also referred to herein as an "exterior surface," "contact wall," "contact surface," "ablation wall," or "ablation surface") 102, the insulation chamber 24 has an exterior wall (also referred to herein as an "exterior surface," "contact wall," "contact surface," "insulation wall," or "insulation surface") 104, and the two chambers 1A, 24 share a single, interior wall 100 disposed between the two chambers 1A, 24 and thereby fluidically separating the two chambers 1A, 24. Alternatively, the two chambers 1A, 24 are separate components that are coupled each other such that the interior wall of the ablation chamber 1A is coupled or otherwise attached to the interior wall of the insulation chamber 24 at 100.

Returning to FIG. 2A, the ablation component 1A has a series of channels 29 defined therein that creates a unidirectional course or pathway laid out through the chamber 1A through which the fluid passes. The channels 29 are defined by the channel walls 19 that are disposed in the pad 1 as shown in FIG. 2A, according to one embodiment. According to one implementation, each of the channel walls 19 are attached to exterior wall 102 of the ablation chamber 1A and extend to and are attached to the interior wall 100 of the chamber 1A such that the walls 19 are fluidically sealed to the exterior 102 and interior 100 walls of the chamber 1A. That is, the walls 19 are attached such that no fluid can pass through the walls 19. As such, the walls 19 are positioned in the chamber 1A and attached as described such that the gas must pass through the channels 29 created by the walls 19. According to one embodiment, the walls 19 are welded, bonded, or otherwise attached to the exterior 102 and interior 104 walls of the chamber 1A. The channels 29 created by the walls 19 create a long pathway within the ablation chamber 1A through which the fluid can pass before exiting the pad 1 via the dedicated outlet line 18. Alternatively, the channels 29 can be created by any known structure or feature in the ablation chamber 1A.

Regardless of the specific structure of the channels 29, the channels are in fluidic communication with each other such that they define a substrate pathway within the chamber 1A in which the substrate travels, advances or flows through the chamber in a pathway that is parallel to the exterior wall 102 of the ablation chamber 1A. In contrast, in certain embodiments, the unidirectional flow of the substrate through the maze-like channels 29 results in the flow of the substrate changing directions within the chamber 1A throughout the pathway. In one embodiment as shown, the channels 29 are disposed adjacent to each other (and in fluidic communication) such that all the channels 29 are substantially parallel to each other and in fluidic communication with one adjacent channel 29 at an end of each channel 29, thereby creating a single, unidirectional pathway. Further, as discussed elsewhere herein, the positioning of the channels 29 such that the exterior wall 102 constitutes one wall or boundary of each channel 29 ensures that the substrate is continuously in contact with the exterior wall 102 as the substrate flows or passes through the chamber 1A. In other words, there is no wasted flow of substrate within the chamber 1A. The channels 29 are each defined by a top surface or wall (the exterior wall 102), a bottom surface or wall (the interior wall 100), and two side walls (which can be two channel walls 19 or a channel wall 19 and a perimeter wall 21, and thus the flow of substrate is a steady flow throughout the chamber 1A and has no dead zones or eddies that influence the distribution of the cold energy on the exterior wall 102. These features can apply to all of the pad embodiments disclosed or contemplated herein.

In certain embodiments, the ablation chamber 1A, in combination with the ablation system to which the pad 1 is coupled (and any ablation pad and/or ablation system embodiment disclosed or contemplated herein), provides for a continuous flow of cooling substrate through the channels 29. As discussed in additional detail below, the continuous flow of the substrate strengthens the ablation energy of the pad 1 and thereby results in a more effective ablation. Further, the greater the flow rate, the greater the ablation energy. In certain embodiments, any ablation chamber embodiment herein in combination with any ablation system herein provides a cooling substrate flowing through the channels (such as channels 29) at a rate of at least 80 L/minute. Alternatively, the flow rate can range from about 40 L/minute to about 120 L/minute. In a further embodiment, the flow rate can be any flow rate that keeps the cooling substrate moving through the ablation chamber 1A. It is understood that this continuous flow feature and these flow rates also apply to any of the ablation chamber embodiments disclosed or contemplated herein.

It is understood that the channels 29 constitute or create a predetermined pathway through the ablation chamber 1A. In certain implementations, the pathway for continuous flow of the cooling substrate can be "maze-like." In one embodiment, the pathway allows for slower transmission of gas through the ablation chamber 1A in comparison to a chamber 1A having no pathways, channels, or other predetermined structures within the chamber 1A.

Further, in certain embodiments, the pathway can also provide symmetric and substantially even distribution of the gas (and thus temperature) through the chamber 1A in a fashion that cannot be accomplished in a structure-less or open chamber. That is, the predefined pathway provides for continuous flow of gas in an even, uniform, or distributed fashion through the chamber 1A, thereby allowing for continuous replacement of warmed gas (as a result of the transfer of energy from the target tissue) with the cold gas being supplied to the chamber 1A by the system 100 and ensuring a fairly constant ablation power along the outer surface of the chamber 1A. That is, according to certain implementations disclosed herein, the continuous unidirectional flow of cooling substrate through a predetermined pathway along the external surface (such as surface 102) within the ablation chamber (such as chamber 1A) results in an ablating surface that cools and cryoablates in a generally uniform fashion. In addition, according to certain embodiments, the unidirectional flow of cooling substrate through a predetermined pathway can provide a substantially potent cryoablation as well, as explained elsewhere herein with respect to the ability of the various pad embodiments herein being able to cryoablate certain tissue despite that tissue having powerful counter-warming action in the form of warm liquid flowing through the tissue. This fairly uniform ablation temperature on the external surface 102 avoids the asymmetry of ablation devices having no such predetermined pathway (such as balloons or bladders) where parts of the ablation surface (pad, chamber, body) become very cold but other parts of the ablation pad never become cold enough to cause ablation of contacted tissue. That is, if the ablation device were a simple inflatable cushion constructed of pliable polymer having a single inflatable chamber with no internal structures or features to create a defined pathway, it would become generally rounded (like a balloon) in response to pressurizing cold gas, with a possible effect of loss of contacted tissue surface due to various external regions of the sphere losing contact with the tissue as a result of the generally rounded shape thereof. In addition, if gas were allowed to flow continuously through such a simple inflatable cushion, there would be very cold regions along the path of least resistance of inflow and outflow along with regions that would not achieve the same low temperatures or ablation power because of stagnant gas flow and thus be less effective at ablation of tissue in the vicinity of such regions.

Of course, it is understood that the temperature of the outer surface (such as surface 102) of the ablation chamber (such as chamber 1A) is not entirely uniform across the entire surface from the start of the gas pathway in the channels (such as channels 29) to the end during use, because the cooling substrate absorbs energy from the target tissue during ablation and thus increases in temperature as it moves through the pathway. As such, there is some temperature difference across the surface of the chamber in the various ablation pad embodiments disclosed or contemplated herein, but the overall surface temperature of each embodiment of the ablation chamber is sufficiently cold across the entire surface to ablate the target tissue successfully. Further, the continuous flow of the cold cooling substrate minimizes the temperature differential.

Additionally, the substantially flat or slightly convex external surface 102 of the ablation chamber 1A results in uniform contact with the target generally flat tissue (in contrast to a rounded surface that results in contact only along the portions of the rounded surface that extend furthest away from the chamber 1A. Plus, in certain embodiments, the walls 19 defining the channel(s) 29 can provide a chamber 1A having less depth (in comparison with a chamber in which the surface is not flat or has no such walls) as a result of the walls 19 minimizing or preventing the expansion or separation of the opposing walls 100, 102 of the chamber 1A, thereby maximizing the contact between the cold gas in the chamber 1A (and thus in contact with the substantially flat outer surface 102 thereof) and the target tissue. That is, the channel walls 19 themselves, by their attachment to the opposing outer walls 100, 102 of the ablation chamber 1A, can operate to minimize or prevent the separation of the opposing outer walls 100, 102 when the chamber 1A is inflated, thereby causing the ablation pad 1 to be generally flat when pressurized with gas. Further, the formation of channels (such as channels 29) that run throughout the entire ablation chamber 1A with one dedicated inlet 17 to the chamber 1A and one dedicated outlet 18 cause a degree of resistance to the flow of gas along this unidirectional pathway that controls the pressure within the channels 29 as well as the rate of gas flow from inlet 17 to outlet 18, allowing sufficient 'dwell-time' of the cooling substrate within the ablation chamber 'maze' (channel pathway) to draw substantial heat from the contacted target tissue, and at the same time, exhaust "spent" substrate that has been warmed as a consequence of this heat transfer out of the chamber 1A via its dedicated outlet or exhaust line 18. This ability to have the cold gas flow in a predetermined path through the chamber 1A continuously and at a predetermined rate as discussed above as opposed to static dwelling (like 'closed' cryoprobes or cryoballoons) or simple chamber pressure/volume maintenance by exchanging small amounts of gas intermittently creates a thermal advantage in terms of potency of tissue freezing in a relatively short period of time. That is, as the very cold substrate in the ablation chamber 1A absorbs energy from contacted tissue, it is warmed and loses potency, but this warmed gas passes through the chamber 1A and exhaust line 18 and thus is continuously—and at a predetermined flow rate—being replaced by a new supply of very cold gas that has yet to absorb heat as a result of the ablation process. In addition, in one embodiment, the configuration of the pressurized channels 29 is engineered to keep the channel heights low enough that much of the flowing cold gas is not 'wasted' by virtue of being too distant from the actual ablating surface 102. In certain implementations, the channel heights are kept low via the channel walls and/or baffle walls in the ablation chamber, as described in additional detail elsewhere herein.

Alternatively (or in addition), the ablation chamber 1A can be constructed of a material—such as a polymer or plastic—that retains a generally flat configuration when inflated or pressurized with the cooling substrate.

In one implementation, the method of creating the channel walls 19 involves the use of a predetermined pattern that is created in an ultrasonic welding unit consisting of a horn and anvil with defined patterns. The channel wall 19 pattern that creates the unidirectional pathway is first created, and then a press plate is created that duplicates that predetermined pattern. In one embodiment, the press plate has a protrusion or ridge extending from the plate for each portion of the channel walls 19. Once the press plate has been engineered and placed in the welding unit, two separate sheets of the desired material for the ablation chamber 1A are positioned appropriately in the unit, and the unit is closed such that the two sheets are positioned between a flat plate and the press plate with the protrusions/ridges. As the two plates are pressed together, the two sheets are ultrasonically welded together at the protrusions, thereby creating the channel walls 19. Alternatively, the device can be any known welding or pressing or other type of device that utilizes a medium such as heat, pressure, ultrasonic waves, or any other known medium for fusing, welding, or otherwise attaching two sheets or forming a chamber in a predetermined pattern that results in a predetermined flow pathway through the resulting chamber.

In certain implementations, as also shown in FIG. 2A, the ablation chamber 1A can also have a plurality of baffle walls 20 disposed in the chamber 1A to decrease or maintain the height of the channels 29 defined in the ablation chamber 1A. Like the walls 19, the baffle walls 20 are attached to exterior wall 102 of the ablation chamber 1A and extend to and are attached to the interior wall 100 of the chamber 1A such that the pressurized walls 100, 102 cannot exceed a predetermined distance (the overall height of the ablation chamber 1A) between the exterior 102 and interior 100 walls of the chamber 1A. The baffles 20 do not fluidically define the channels 29 through the chamber 1A, but instead are interrupted or discontinuous walls 20 within the channels 29 as shown. The baffles 20 are welded, bonded, or otherwise attached to the exterior 102 and interior 100 walls of the chamber 1A. Such baffles do not contribute to or increase the resistance of flow through the unidirectional channel pathway created by the channels 29, but rather hold or maintain the channels 29 between exterior 102 and interior 100 walls at a predetermined height when pressurized with gas or liquid, thereby preventing the two walls 100, 102 from separating or increasing in distance from each other when gas is forced into the chamber 1A. By restricting the maximum height of the chamber 1A between the exterior 102 and interior 100 walls, a predetermined distance that cannot increase is maintained between the target tissue and the gas flowing through the pad 1, thereby ensuring maximum impact of the gas flowing through the chamber 1A and ensuring that most or all gas passing through the chamber 1A is in relatively close contact with the target tissue and thereby has the ability to absorb energy. In other words, maintaining or reducing the amount of space between the exterior 102 and interior 100 walls in the chamber 1A via the channel walls 19 and the baffles 20 reduces or eliminates any "wasted" gas that might otherwise flow or stagnate in a location more distant from the contact surface 102 of the ablation chamber 1A.

FIG. 3A is another aerial view of the ablation chamber 1A of the pad 1. In this embodiment, the ablation chamber 1A contains a plurality of sensors 22 on the contact surface 102. The various sensors 22 can be, in accordance with certain implementations, different sensors 22 that are configured to monitor various different parameters within the ablation chamber 1A of the pad 1. In one embodiment, the sensors 22 can be positioned on the outer surface of the contact surface 102 of the pad 1 as shown and used to monitor metrics such as temperature and voltage to facilitate the procedure. Alternatively, the sensors 22 (or other sensors) can be positioned on the inner surface of the contact surface 102 of the pad 1 and used to monitor metrics within the chamber 1A. In a further implementation, a similar sensor array (not shown) can be positioned on the outer surface (or inner surface) of the exterior wall 104 of the insulation chamber 24.

Voltage sensors on the contact surface 102 of the ablation chamber 1A can be used to confirm that the ablation portion of the device is in proper contact with the target tissue. For example, in one implementation, if the ablation pad 1 is positioned incorrectly in certain areas, zero voltage may be sensed. In that implementation, contact force (piezoelectric) sensors may be used, as described in further detail below Further, temperature sensors can be used to confirm that desired target (very low) temperatures are achieved on the surface of the pad where tissue is contacted.

It is understood that the ablation pad (such as pad 1 or any other pad embodiment disclosed or contemplated herein) is made of polyurethane, polytetrafluorethylene ("PTFE") (such as, for example, Teflon®), polyimide (such as, for example, Kapton®), or any other known, pliable medical grade polymer or plastic such that it can be expanded from a collapsed or uninflated configuration into a deployed or inflated configuration.

In one embodiment, the ablation pad 1 (or any other pad embodiment herein) has an overall footprint (or "pad print") of its external surface 102 that takes the shape of a rectangle. In one specific example, the external surface 102 is about 6.5 cm long and about 2.5 cm wide with rounded edges. Alternatively, the external surface 102 can have any known dimensions and any known shape for use in an ablation procedure.

It is further understood that the external surface 102 (or any external surface of any pad embodiment herein) is substantially flat or convex, as discussed elsewhere herein. That is, the external surface 102 can be not only flat, but also slightly rounded when the pad (such as pad 1) is in its deployed or inflated configuration without any external forces from any target tissue or surrounding tissue being applied thereto.

FIG. 3B depicts the controller 27 with the GUI, according to one embodiment. As discussed above, the controller 27 has system controls and monitors temperatures and voltages throughout the system 100, including on the exterior surface of the exterior wall 102 of the pad 1. In addition, the control can also have safety and quality control monitoring as needed.

In certain embodiments, as mentioned above, the cooling substrate is helium or hydrogen and can be used in any system and/or ablation pad embodiment disclosed or contemplated herein. One major hurdle for typical known cryoablation systems is the specific thermal problem of ablating cardiac tissue that is being actively warmed by flowing blood inside the heart. The known devices generally utilize a highly pressurized gas (usually argon or nitrous oxide) that has adequate thermal conductivity (which roughly translates to the energy (heat) absorptive capacity of a particular gas) to ablate static tissue that is not being actively warmed by flowing blood, but is not as successful ablating tissue that is being actively warmed. Further, this difficulty (relating to actively warmed tissue) becomes more challenging as the size of the tissue area to be ablated increases. In contrast, helium and hydrogen, for example, have thermal conductivities that are in the range of 10 times greater than that of argon and nitrous oxide. As such, helium or hydrogen as cooling substrates are very effective in cooling and ablating tissues that are being actively warmed. Helium, for example, is an effective cooling substrate that is generally safe, non-flammable, non-reactive, and non-toxic.

In certain embodiments, in this pad 1 or in any other pad embodiment herein, temperature and gas flow sensors (not shown) can also be positioned in one or more locations in the inlet 17 and outlet 18 gas pathways. Wattage actually withdrawn from the target tissue can be measured indirectly using these sensors (not shown) by having the controller (such as controller 27 above) calculate gas flow rates and temperature drop over time from the inlet 17 sensors to the outlet 18 sensors. In such a fashion, dynamic adaption of the time of ablation can be tailored to the individual patient, since atrial wall thickness and fatty tissue coverage can vary. That is, the wattage being taken from the tissue can be calculated by tracking the temperature drop and the flow rate as discussed above. The wattage can provide information about ablation success, which can vary from patient to patient based on various factors. Thus, the wattage information can be used to adjust the ablation time or other adjustable variables, thereby tailoring the treatment to the specific patient.

In a further implementation, a mapping and insulation device is provided herein, rather than (or in addition to) an ablation and insulation device. That is, instead of (or in addition to) ablation, the device is a substantially flat pad with an insulation chamber (substantially similar to the insulation chamber embodiments herein) and various sensors such as those discussed above that can be used for surface mapping. In one embodiment, the mapping pad could be positioned in contact with an external atrial wall of the patient's heart (with the insulation chamber positioned between the mapping surface and other tissues around the heart) such that the surface of the heart could be monitored while an ablation procedure is performed inside the heart. The mapping pad could be used to identify any electrically active portions of the heart tissue and thus identify the target portions of the tissue for ablation using a standard ablation tool for use in an interior chamber of the heart. In one implementation, an ablation pad according to any embodiment disclosed or contemplated herein could be used to ablate the target exterior surface of the heart, and then the mapping pad could be used to identify any portions of that tissue not successfully ablated so that interior ablation can be used. In addition, according to certain embodiments, the mapping pad with the insulation chamber also makes it possible to be more aggressive with the interior ablation, because the insulation chamber can provide protection to any other tissues or organs around the heart. Alternatively, such a mapping device can be used to map and/or ablate any target tissue.

FIG. 4A shows one embodiment of the ablation pad 1, which is a rolled-up or folded-up version of the ablation/insulation device 1 for minimally invasive delivery to the target tissue. In this example, the surface of the ablation chamber 1A is mostly hidden in this illustration by virtue of folding. The inlet 17 and outlet 18 lines are coupled to the ablation chamber 1A as discussed above for gas exchange. Also depicted is the un-expanded insulation chamber 24 that lies immediately adjacent to or "underneath" the ablation chamber 1A.

FIG. 4B shows a partially expanded ablation device 1, with the upper, ablation pad 1A on the surface, facing up, being rolled out and unfurled side to side as depicted by arrows 26. Also seen here is a partially expanded insulation chamber 24, being filled with air or another gas (such as, for example, argon) via inflation line 25. According to one embodiment, the insulation chamber 24 is filled to a predetermined filling pressure. Barrier or wall 23 is the wall that separates the upper ablation pad 1A and the lower insulation chamber 24. In this example, it is the inflation of insulation chamber 24 that unfurls or deploys the ablation pad 1A so that the pad 1 can then be positioned in contact with a target flat tissue surface for ablation (not shown).

An ablation pad 1 is depicted in FIGS. 5A-5C, according to one embodiment. FIG. 5A shows a top/right perspective view of the device 1, with the ablation chamber 1A depicted as the upper (top) chamber 1A, and the uninflated insulation chamber 24 below it. Also depicted are dedicated inlet 17 and outlet 18 fluid lines coupled to the upper (ablation) pad 1A, and insulation chamber inflation line 25 coupled to the insulation chamber 24.

FIG. 5B depicts the same perspective view of the pad 1 as depicted in FIG. 5A, while FIG. 5C is a perspective view of the underside or insulation chamber 24 side of the pad 1. The insulation chamber 24 is inflated via the inflation line 25 coupled thereto, and in this specific example, the chamber 24 has a predetermined and structured height, which is the distance between the interior wall 100 and the exterior wall 104 of the insulation chamber 24, as best described above and depicted in FIG. 2B. That is, the height of the insulation chamber 24 is substantially symmetrical and consistent, especially along the periphery of the pad 1, creating a substantially flat structure for the ablation pad 1 without any significant bends or curves. According to certain embodiments, the controlled or structured flat configuration of the insulation chamber 24 is accomplished with the baffle walls 28 formed in the chamber 24. Alternatively, in those implementations without baffle walls, the controlled or structured flat configuration of the chamber (such as chamber 24) is accomplished with the channel walls, as described elsewhere herein). In further embodiments, the baffle walls 28 and channel walls work together to help maintain the controlled or structured flat configuration. The baffle walls 28 are visible in FIGS. 5B and 5C and form clefts or indentations on the exterior wall 104 of the insulation chamber 24. In FIG. 5C, the baffle walls 28 are shown as indentations in the exterior wall 104 of the chamber 24, wherein the exterior wall 104 of the chamber 24 has been welded, bonded, or otherwise attached to the interior wall 100 of the chamber 24, thereby forming the baffle walls 28 that appear as clefts or indentations as shown. The walls 28 create more symmetrical distribution of air within the insulation chamber 24 and thereby more consistent height of the chamber 24 across the length and width of the chamber 24, including its periphery. In several embodiments, the height of the insulation chamber 24, when inflated, is a multiple of the height of the ablation chamber 1A. For example, in one implementation, the height of the inflated insulation chamber 24 is at least one inch. According to certain embodiments, the exterior wall 104 can be a double-layer wall 104.

It is understood that, in the various ablation pad embodiments disclosed or contemplated herein, the insulation chamber (such as chamber 24 discussed above) must protect other tissue in the vicinity that is not targeted for ablation (everything but the target tissue). This is accomplished by both displacing or otherwise moving the target tissue away from adjacent, non-target tissues, as well as by creating an insulating structure within or via this chamber that has poor thermal conductivity. The poor thermal conductivity can be accomplish in certain exemplary embodiments by providing poor thermal conductors such as air or room temperature argon in the chamber (such as chamber 24). Another aspect of this insulation chamber, according to certain embodiments, is that the displacement of the ablation pad should be generally symmetrical (rather than a spherical shape, for example), as discussed above with respect to FIGS. 5A-5C. In order to overcome this limitation, various embodiments (such as the chamber 24 in FIGS. 5A-5C) herein create more symmetrical displacement. Another embodiment utilizes an insulation chamber made of multiple inflatable cushions or balloons in a style of pontoons, to assure that displacement occurs symmetrically underneath the planar ablation pad.

Figure 7A:
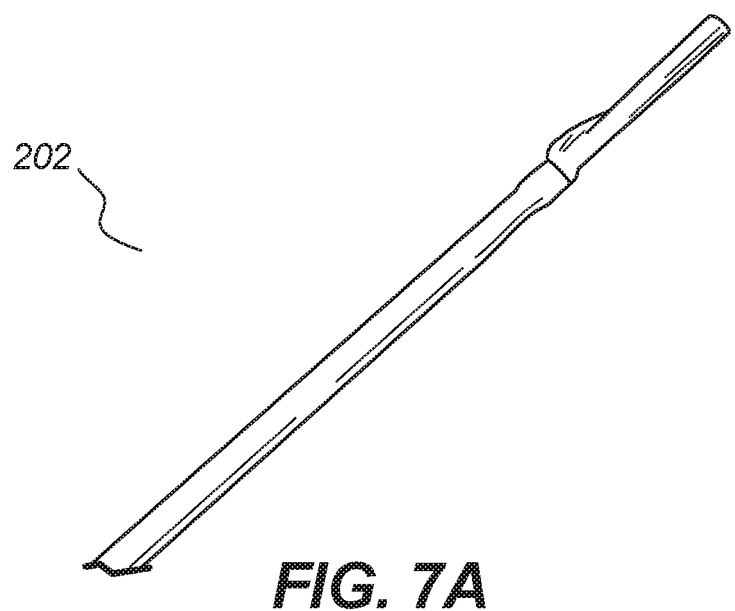
FIG. 7A is a perspective view of a sheath that can be used to deploy an ablation pad during a procedure, according to one embodiment.
Figure 7B:
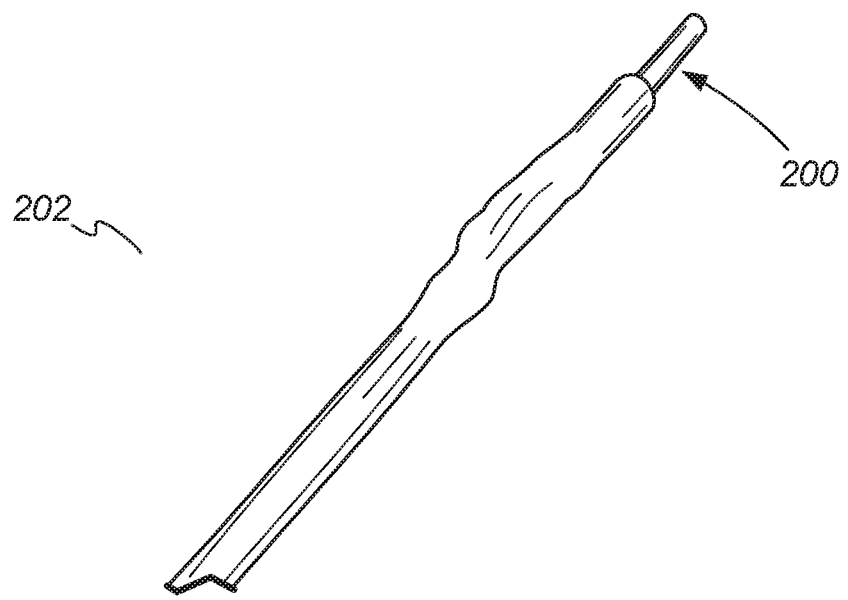
FIG. 7B is a perspective view of the sheath of FIG. 7A with the ablation pad being urged distally out of the distal end of the sheath, according to one embodiment.
Figure 7C:
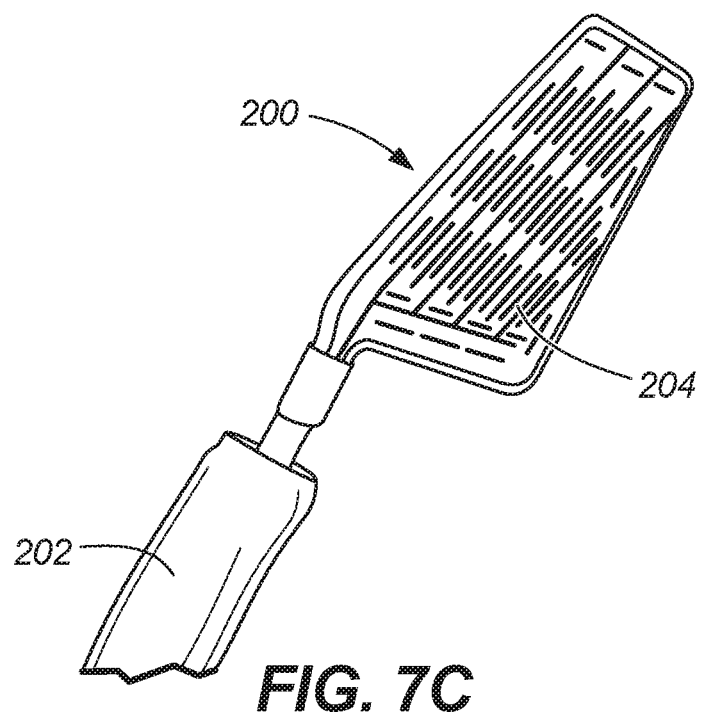
FIG. 7C is a perspective view of the sheath of FIG. 7A with the ablation pad deployed therefrom, according to one embodiment.
Figure 7D:
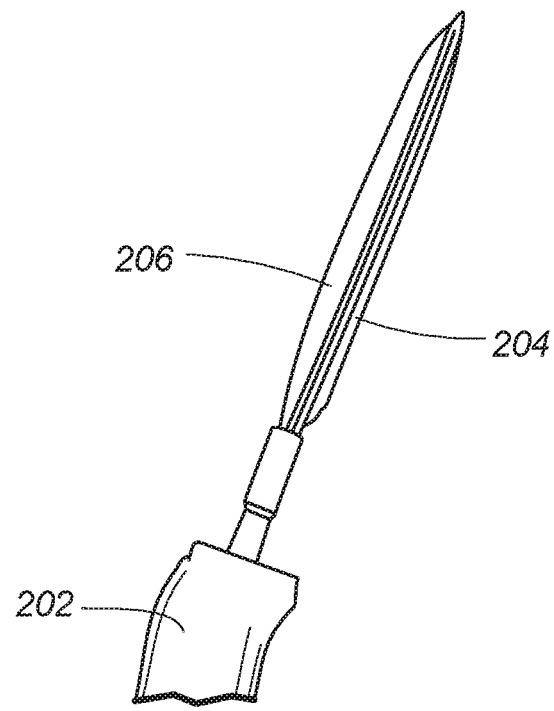
FIG. 7D is a side view of the sheath and ablation pad of FIG. 7C, according to one embodiment.
Figure 7E:
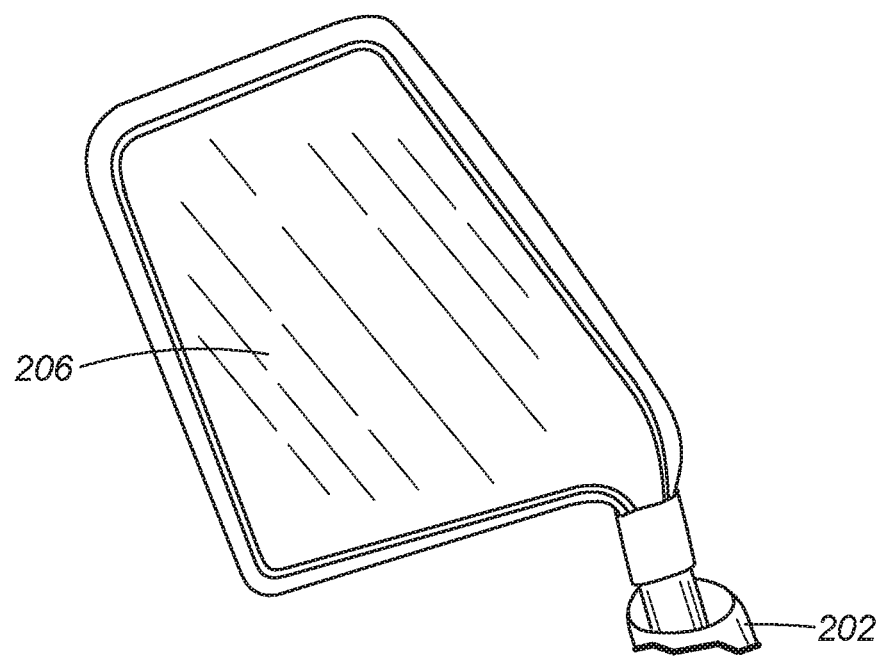
FIG. 7E is a plan view of the sheath and ablation pad of FIG. 7C, according to one embodiment.

Another exemplary implementation of a pad 200 for use in the systems contemplated herein is depicted in FIGS. 7A-7E, which show that the pad 200 can be deployed out of a sheath 202. More specifically, FIG. 7A depicts the sheath 202 with the pad 200 deployed therein (not visible in the figure). The pad 200 is then urged distally out of the distal opening of the sheath 202 as shown in FIG. 7B until the pad 200 deploys into its deployed configuration as shown in FIG. 7C. As best shown in the side view of FIG. 7D, the pad 200 has an ablation surface 204 and an insulation surface 206 as shown.

Another example of an ablation system into which the various improvements and additional features of the instant application could be added is provided in U.S. application Ser. No. 14/772,654, filed on Sep. 3, 2015 and entitled "Action/Counteraction Superimposed Double Chamber Broad Area Tissue Ablation Device," which is incorporated herein by reference in its entirety.

In use, the pad 200 (or pad 1 or other ablation component embodiments as contemplated herein) can be used in a minimally invasive, non-transvenous procedure in which the pad 200 (or pad 1 or any other pad embodiment disclosed or contemplated herein) is delivered to an outer (epicardial) surface of the heart and expanded from a collapsed configuration to come into contact with an epicardial surface such as the epicardial surface of the posterior left atrium, the right atrial free wall, or a portion of one of the ventricles. Alternatively, the device can be delivered to any target tissue or organ in a similar fashion. In a further alternative, the device can be delivered via any known approach or procedure.

Figure 8:
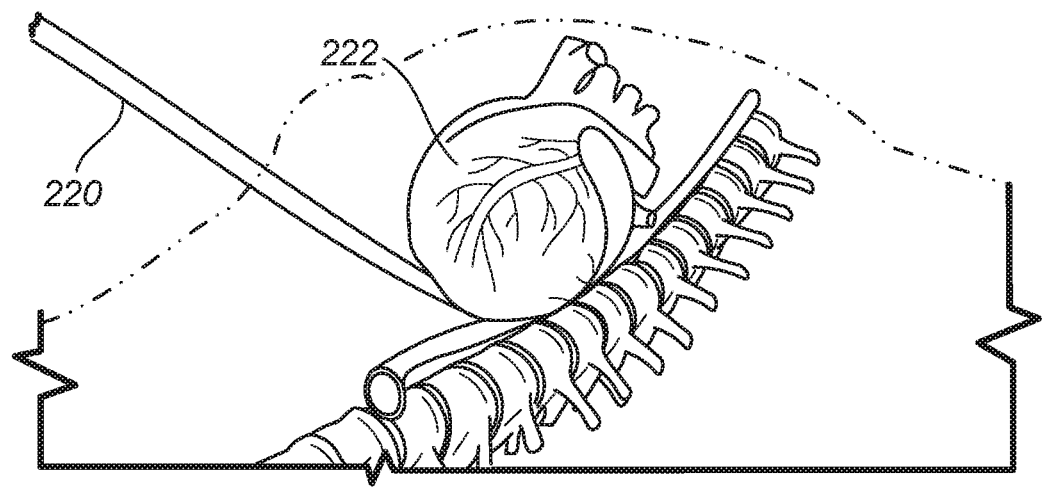
FIG. 8 is a cross-section view of a portion of a patient's chest cavity with an access tube being inserted therein for an ablation procedure, according to one embodiment.
Figure 9:
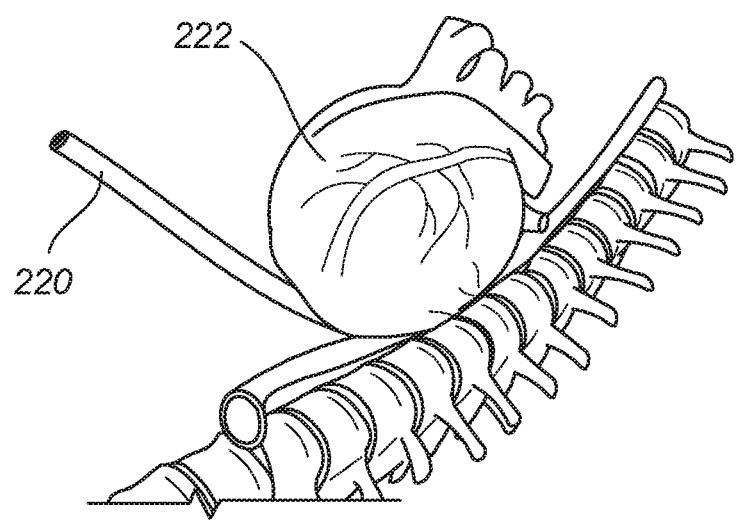
FIG. 9 is a cross-section view of the chest cavity of FIG. 8 in which the access tube is positioned "beneath" the left atrium of the heart, according to one embodiment.
Figure 10:
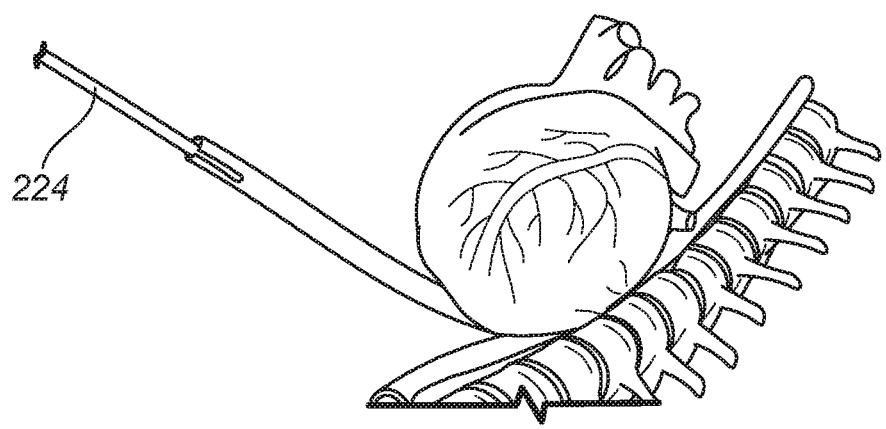
FIG. 10 is a cross-section view of the chest cavity of FIG. 8 in which the sheath is inserted through the proximal end of the access tube, according to one embodiment.
Figure 11:
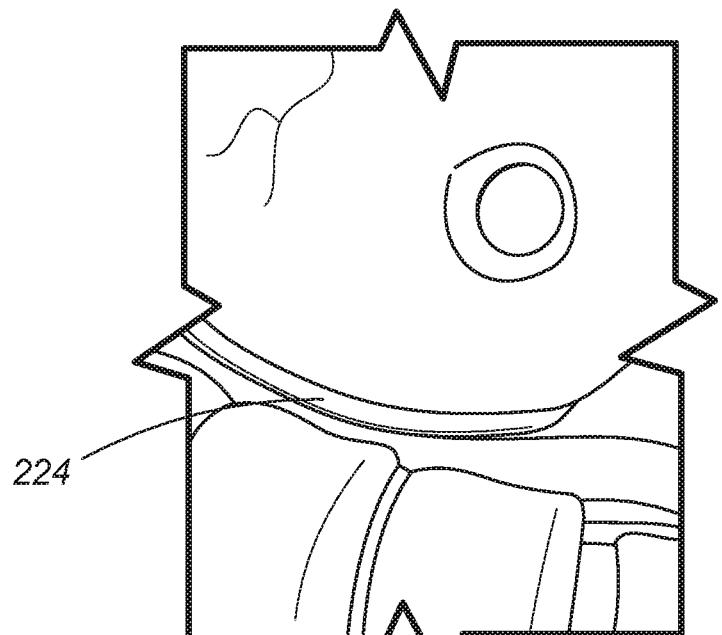
FIG. 11 is a cross-section, expanded view of a portion of the chest cavity of FIG. 8 in which the sheath is extended out of the distal end of the access tube, according to one embodiment.
Figure 12:
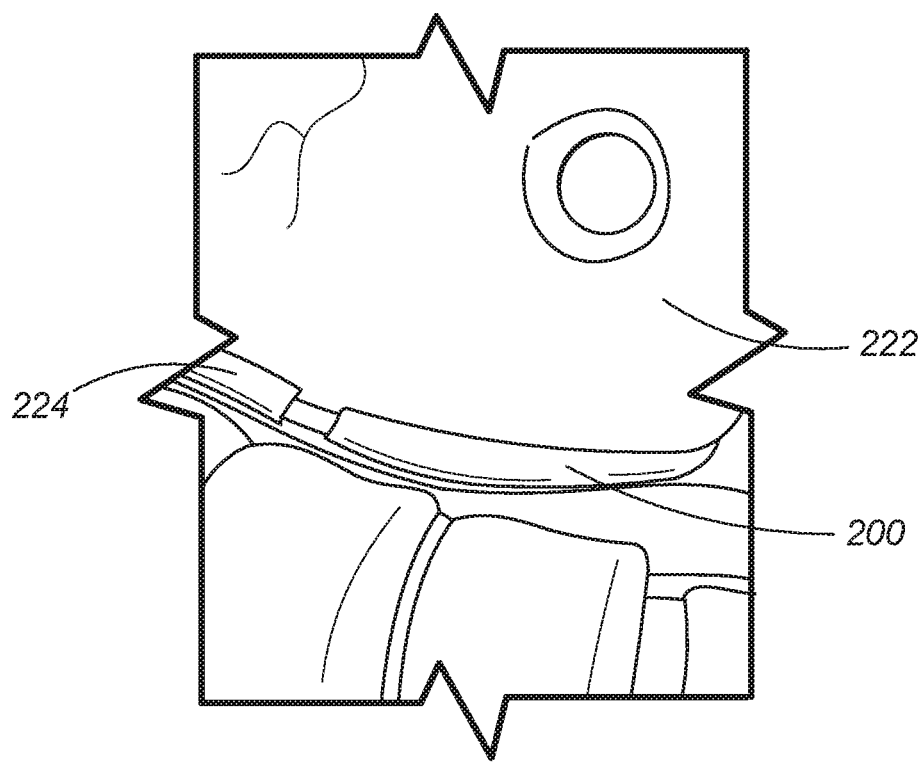
FIG. 12 is a cross-section, expanded view of a portion of the chest cavity of FIG. 8 in which the ablation pad is extended out of the distal end of the sheath, according to one embodiment.
Figure 13:
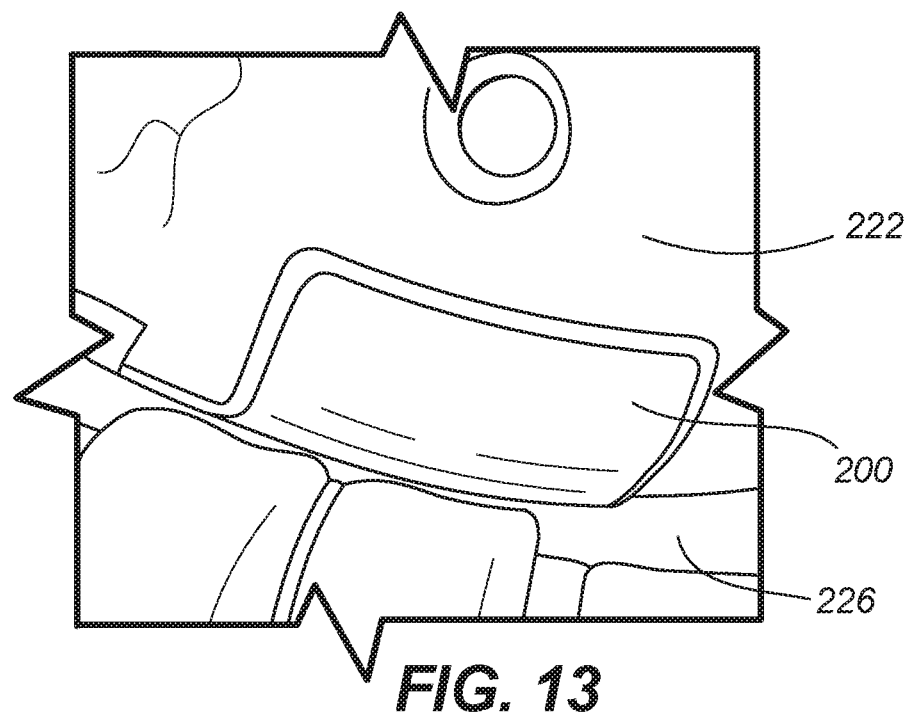
FIG. 13 is a cross-section, expanded view of a portion of the chest cavity of FIG. 8 in which the ablation pad is deployed, according to one embodiment.

For example, an ablation procedure can be performed using the pad 200 (or pad 1 or any other pad embodiment) in the following manner as shown in FIGS. 8-22, according to one specific implementation. First, a small incision is made just below the breastbone of the patient, and the space surrounding the heart is entered with an access tube 220 using video guidance, as shown in FIG. 8. The distal end of the access tube 220 is positioned beneath the left atrium of the heart 222 as shown in FIG. 9. The sheath 224 containing the pad 200 is then inserted through the access tube 22 as shown in FIG. 10 and extended out of the distal end of the tube 222 as shown in FIG. 11. Once the sheath 224 is positioned as desired, the pad 220 is urged distally out of the distal end of the sheath 224 (or the sheath 224 is retracted while the pad 220 is held in place), thereby resulting in the pad 220 being positioned against the left atrium of the heart 222 in its undeployed configuration as shown in FIG. 12. The pad 200 is then deployed into its deployed configuration, typically by inflation, as shown in FIG. 13. The inflation urges the ablation surface 204 into contact with the back wall of the left atrium of the heart 222 while simultaneously creating an insulating cushion to prevent injury to adjacent structures such as the esophagus 226.

Figure 14A:
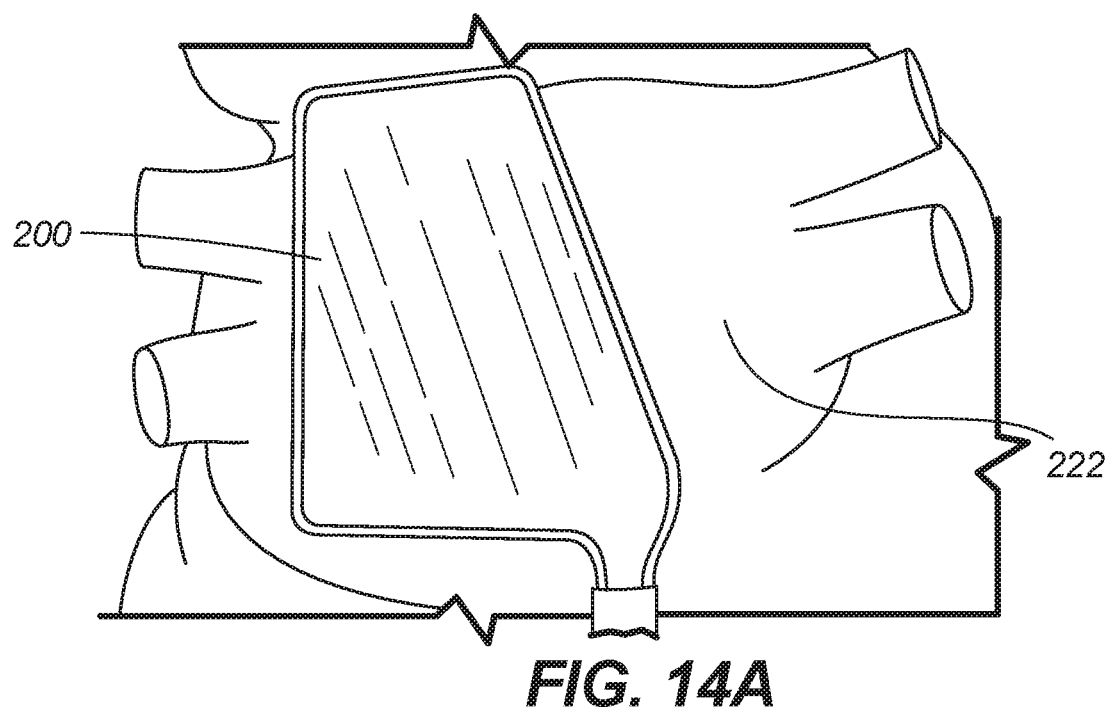
FIG. 14A is a front, expanded view of the ablation pad positioned against the patient's heart, according to one embodiment.
Figure 14B:
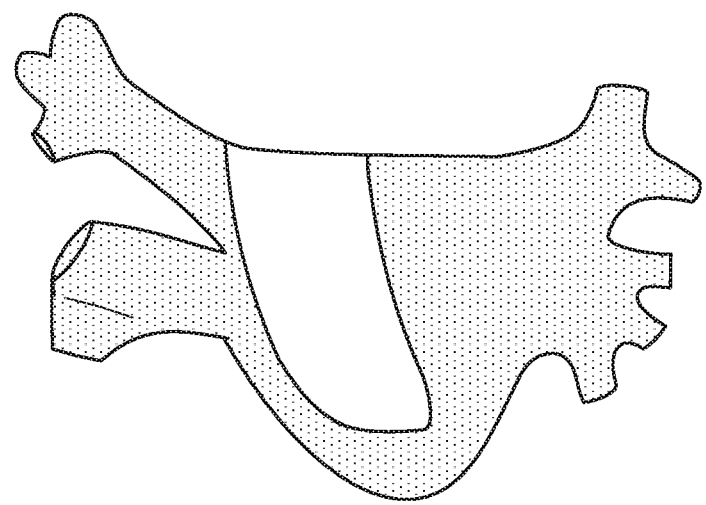
FIG. 14B is a front, expanded view of the patient's heart after ablation of a portion thereof, according to one embodiment.

Another perspective of the pad 200 positioned against the left atrium of the heart 222 is shown in FIG. 14A. At this point, the sensors (not shown) on the ablation surface 204 in this embodiment can be used to create a detailed voltage map to guide the ablation process. Once the map is created, ultra-cold gas (the cooling substrate) is circulated through the channels (not shown) of the ablation chamber (not shown) of the pad 200 and is continuously replenished by the proprietary flow-through design, resulting in robust ablation power. It is understood that the channels and ablation chamber can be any of the channel or ablation chamber embodiments disclosed or contemplated herein. Integrated temperature sensors (not shown) in the pad 200 can also, according to certain implementations, confirm uniform cooling as the pad 200 adheres to the atrium of the heart 222 during freezing. Thus, it is understood that, according to certain embodiments, sensor analysis can facilitate tissue ablation, and in specific instances, assure adequate tissue ablation. The area of the outer surface of the left atrium that is ablated is shown in FIG. 14B.

Figure 15:
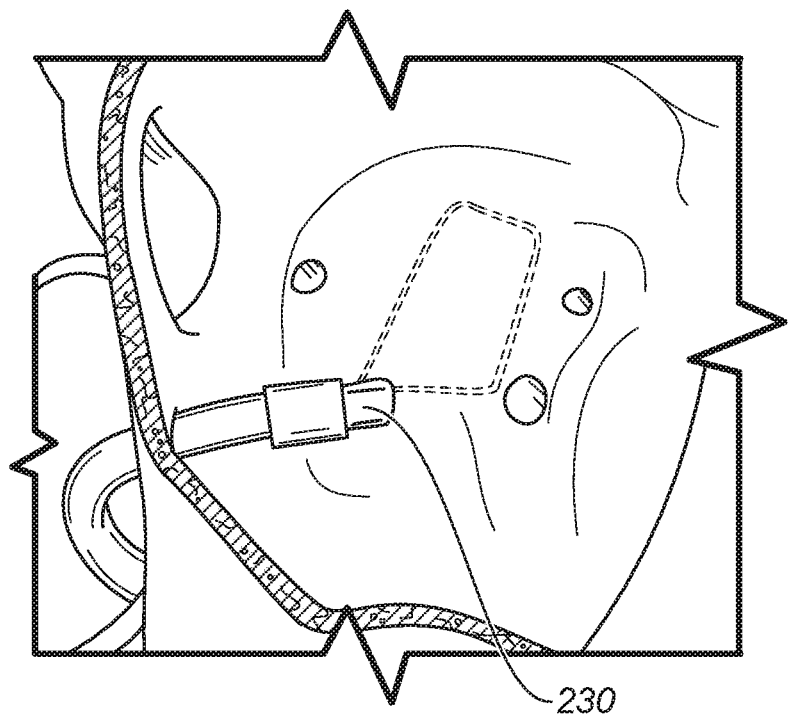
FIG. 15 is a cross-section, expanded view of an inner portion of the patient's heart in which a catheter ablation device is disposed therein, according to one embodiment.

In accordance with one embodiment, a separate catheter ablation step using a catheter ablation device 230 can be performed simultaneously or concurrently by positioning the catheter ablation device 230 inside the left atrium as shown in FIG. 15.

Figure 16A:
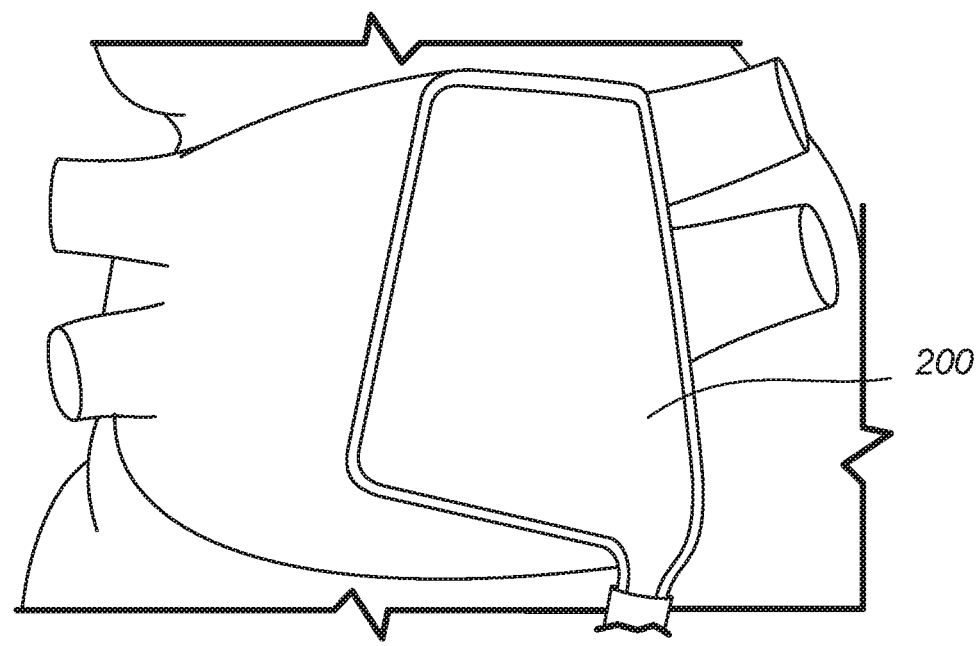
FIG. 16A is a front, expanded view of the ablation pad positioned against another portion of the patient's heart, according to one embodiment.
Figure 16B:
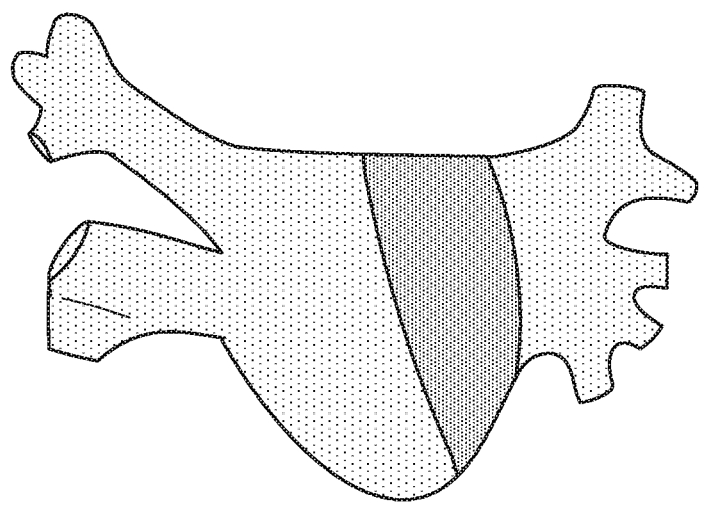
FIG. 16B is a front, expanded view of the patient's heart after ablation of a portion thereof, according to one embodiment.

In accordance with one implementation, relatively warm gas (the warming substrate) is then circulated through the ablation chamber (not shown), causing the pad 200 to thaw quickly and thereby separate from the tissue of the heart 222, thus allowing for safely re-positioning away to another target ablation area on the outer surface of the heart 222 as shown in FIG. 16A. The above steps can then be repeated to ablate the new target ablation area, as shown in FIG. 16B.

It is understood that, according to alternative embodiments of any of the various ablation systems or processes disclosed or contemplated herein, ablation via a cooling substrate (such as cold gas, including, for example, helium) can be followed by application of a warming substrate (such as warmer gas, including, for example, room temperature gas). That is, once an ablation cycle is deemed to be complete, and the cooling substrate (such as helium) flow is terminated, a warming substrate, such as helium gas is provided. In certain implementations, the thawing gas is passed through a warmer or warming device such as, for example, a Joule-Thomson device. Alternatively, any known warming device for warming gas can be used. The thawing substrate is intended to warm the ablation pad, which has a dual effect of exacerbating ablation (rapid cooling followed by heating) and also allows reversal of cryoadhesion of the ablation pad, which will typically remain firmly attached to the target atrium wall well after the argon flow has been terminated. This will make it easier and quicker to either re-position the device for a next ablation or to withdraw the device as the procedure is being terminated.

Figure 17:
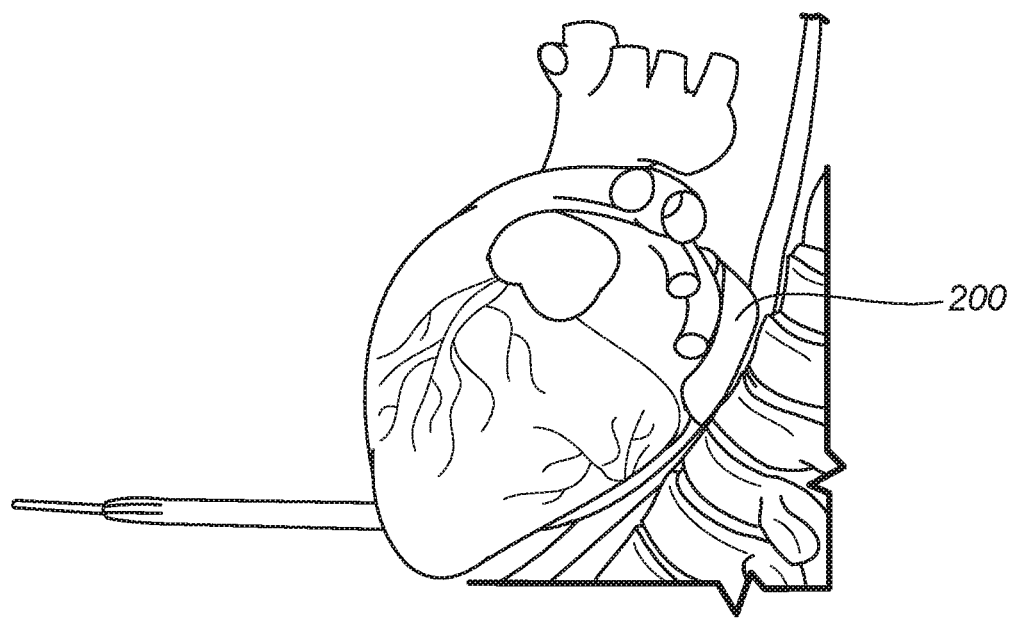
FIG. 17 is a cross-section, expanded view of a portion of the chest cavity of FIG. 8 in which the ablation pad is prepared for retraction, according to one embodiment.
Figure 18:
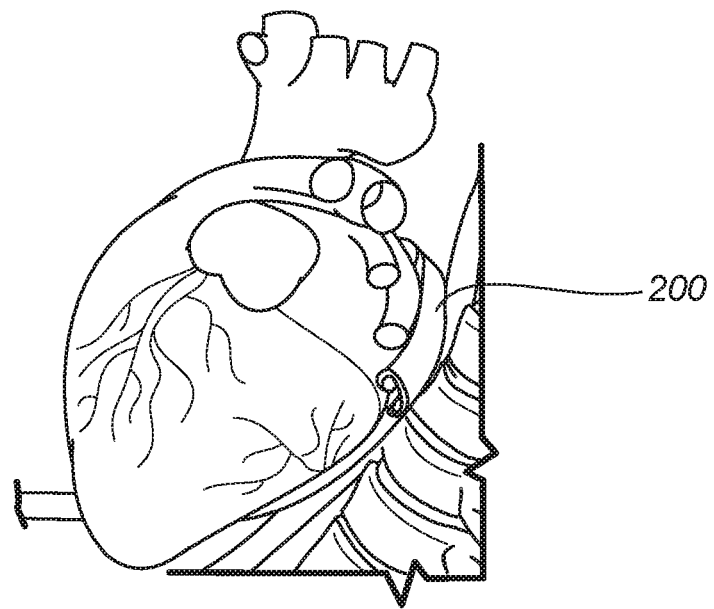
FIG. 18 is a cross-section, expanded view of a portion of the chest cavity of FIG. 8 in which the ablation pad is moved into its retracted configuration, according to one embodiment.
Figure 19:
FIG. 19 is a cross-section, expanded view of a portion of the chest cavity of FIG. 8 in which the ablation pad is retracted into the sheath, according to one embodiment.
Figure 20:
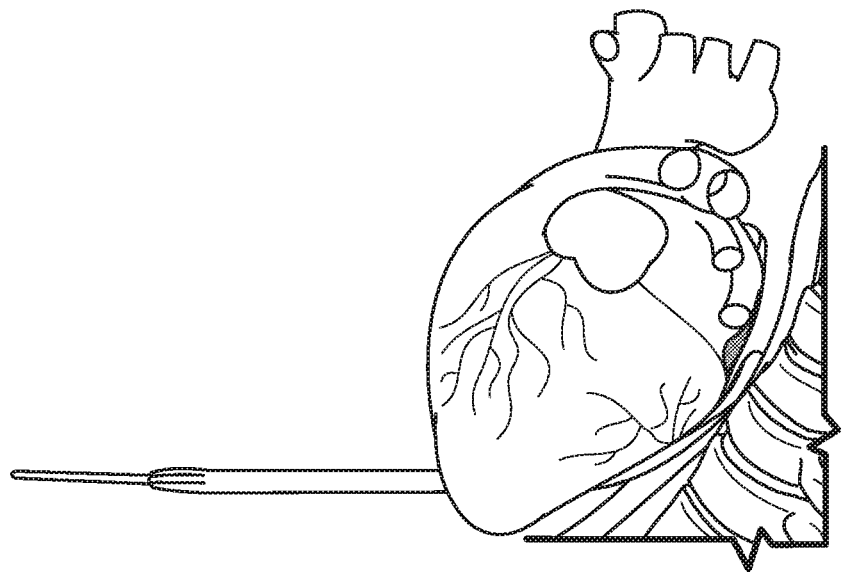
FIG. 20 is a cross-section view of a portion of the chest cavity of FIG. 8 in which the ablation pad is retracted into the sheath, according to one embodiment.
Figure 21:
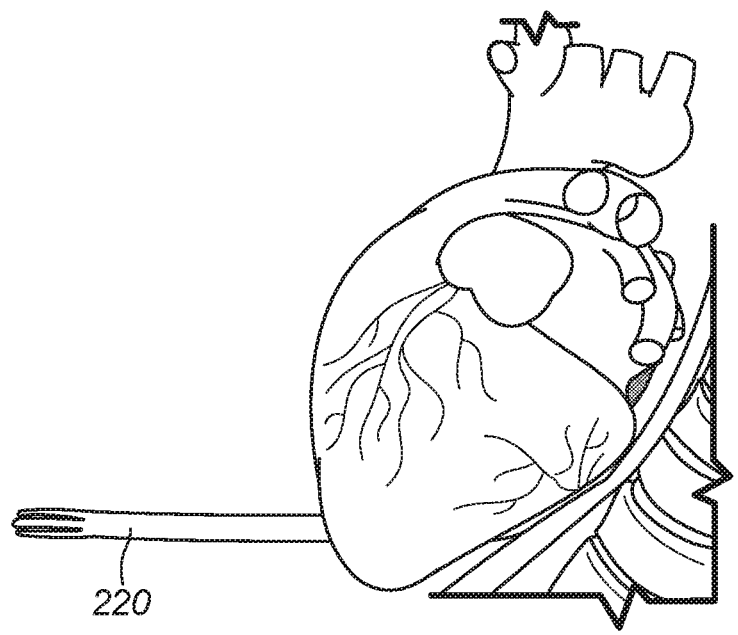
FIG. 21 is a cross-section view of a portion of the chest cavity of FIG. 8 in which the sheath is retracted from the access tube, according to one embodiment.
Figure 22:
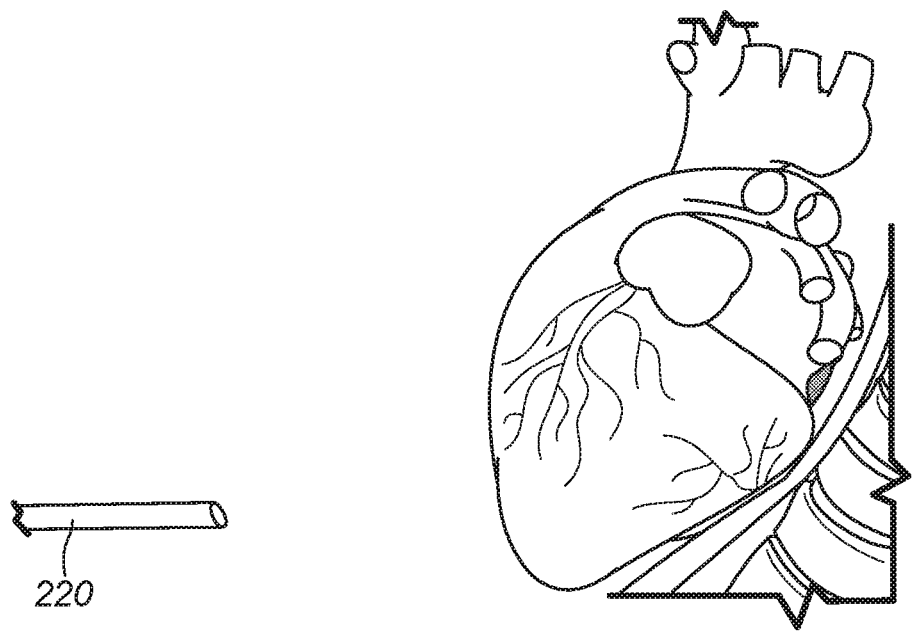
FIG. 22 is a cross-section view of a portion of the chest cavity of FIG. 8 in which the access tube is retracted from the patient, according to one embodiment.

Once the ablation process is complete, the pad 200 as shown in FIG. 17 can be prepared for retraction. First, the pad 200 is caused to move into its undeployed or retracted configuration as shown in FIG. 18. The pad 200 is then retracted into the sheath 202 as shown in FIG. 20. The sheath 202 (containing the pad 200) is then retracted from the access tube 220 as shown in FIG. 21. And then the access tube 220 is removed from the patient as shown in FIG. 22.

It is understood that other methods can be used to ablate an outer surface of an organ using the pad 200 or any other pad embodiment disclosed or contemplated herein.

Certain system and device embodiments as disclosed or contemplated herein incorporate helium as a cooling substrate in a cryoablation application. In those implementations, the systems utilize a mechanism other than a Joule-Thomson orifice to cool the helium, as will be described in further detail herein. As an example, in certain embodiments, the helium enters the ablation chamber of the ablation pad at an inlet pressure of approximately 1.5 standard atmospheres ("atm") and a temperature close to −180° to −190° C. In the various system and device embodiments disclosed or contemplated herein in which the ablation substrate (also referred to herein as "coolant substrate" or "cooling substrate") is helium, the system or device cools the helium to a temperature ranging from about −200° C. to about −150° C. Alternatively, the helium is cooled to a temperature ranging from about −175° C. to about −195°. In further alternatives as mentioned above, the temperature ranges from about −180° to about −190° C. In certain embodiments, the cooling substrate—such as helium—can enter the ablation chamber at an inlet pressure of about 40 psi or less. Alternatively, the cooling substrate can enter at an inlet pressure of about 15 psi or less.

Figure 23:
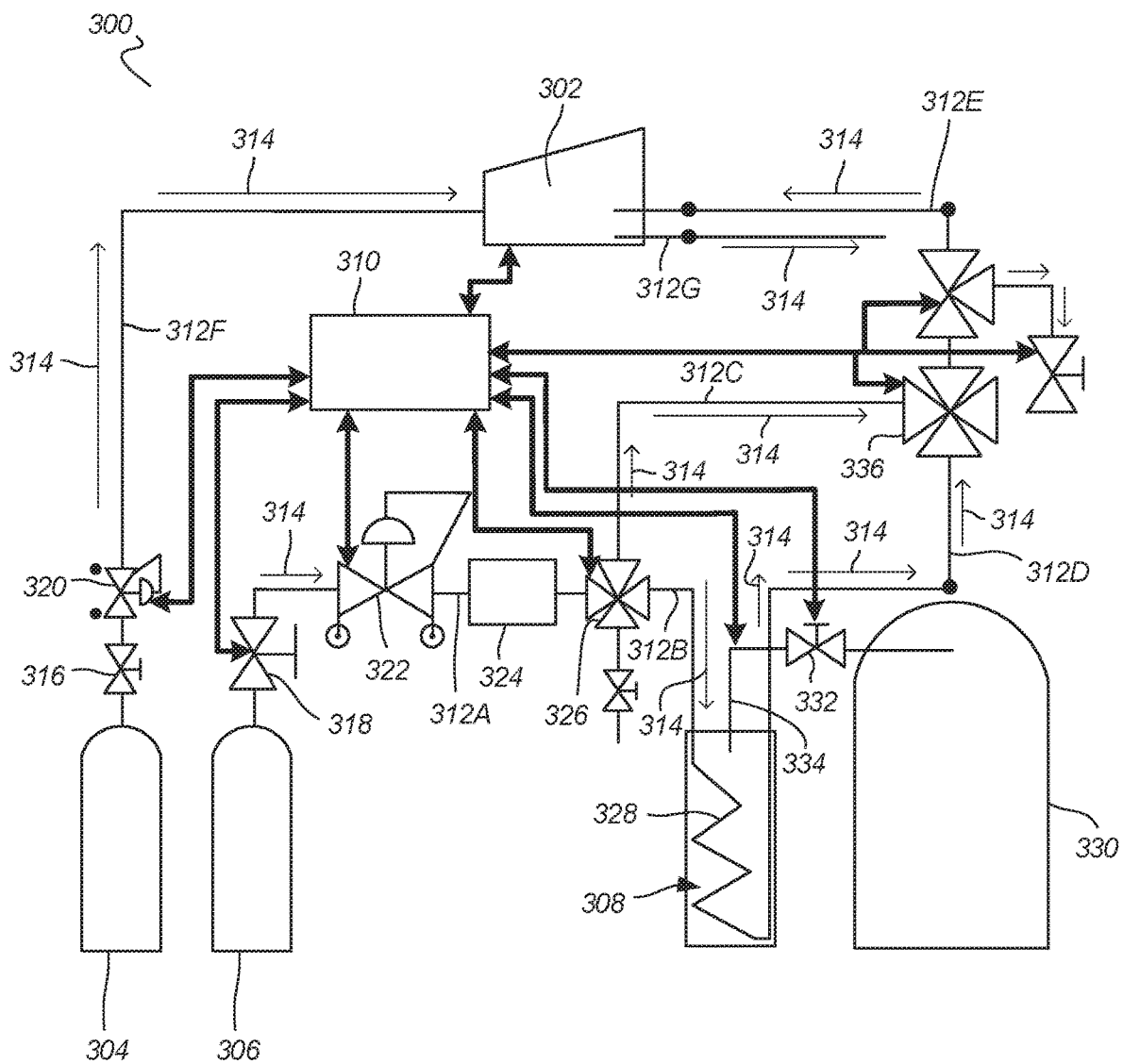
FIG. 23 is a schematic view of an ablation system, according to another embodiment.

Another ablation system 300 is depicted according to another embodiment in FIG. 23. This exemplary system 300 has an ablation pad 302, two pressurized cylinders of gas 304, 306, a cooling (or "chilling") device 308, and a controller 310. Further, the system 300 has fluid lines (or "substrate lines" or "gas lines") 312 extending between the various components of the system 300 as will be discussed in further detail below, with the fluid typically traveling within the lines 312 in the direction indicated by arrows 314. The specific fluid lines 312 will be discussed in further detail below.

In one implementation, standard check-valves 316, 318 are coupled to the cylinders 304, 306 and are used for safety and containment purposes. When opened, the valves 316, 318 allow the substrate to flow through a pressure regulator 320. One of the pressurized cylinders of gas 304 provides the insulating substrate (such as air or argon, for example) to the insulating chamber (not shown) in the ablation pad 200. Further, the other cylinder 306 provides the cooling substrate in the form of a gas. In one specific embodiment, the gas is helium. Alternatively, the gas can be hydrogen, argon, nitrogen, or any other known gas that can be used as a cooling substrate. Further, one or both of the gas cylinders 304, 306 can also provide a warming substrate in the form of a different gas to be supplied to the pad 302 after application of the cold gas. For example, the warming substrate can be helium and also originate from pressurized cylinder 306, or, alternatively, it can be any other known warming substrate. Alternatively, the system 300 can have only one cylinder. In a further alternative, the system 300 can have three or more cylinders.

In the specific implementation depicted in FIG. 23, the system 300 has a first cylinder 304 containing argon (or any other known insulating substrate) and a second cylinder 306 containing helium (or any other known cooling substrate). In this embodiment, the valve 316 allows argon to flow from the cylinder 304 through a pressure regulator 320, along an insulating substrate delivery line 312F and into the insulation chamber (not shown) of the ablation pad 302. In certain embodiments, the argon in the cylinder 304 is room temperature. The valve 318 allows helium to flow from the cylinder 306 through a pressure regulator 322 along a cooling substrate delivery line 312A. In one specific embodiment, the helium flows through a flow meter 324, through bypass valve 326, and through the cooling chamber intake line 312B to the cooling chamber 308.

In one specific embodiment, the cooling chamber 308 has a coiled tube 328 disposed within a coolant within the chamber 308, such that the helium flows through the coiled tube 328. In this specific implementation, the coolant is liquid nitrogen that flows from an insulated container (or "dewar") 330 through a valve 332 along a coolant delivery line 334 and into the chamber 308. As such, the helium flowing through the coiled tube 328 flows through the liquid nitrogen and is cooled as a result. That is, the very cold temperature of the liquid nitrogen causes the temperature of the helium to drop, thereby resulting in the substantial cooling of the helium. In one specific embodiment, the liquid nitrogen is maintained in the insulated storage container 330 at a temperature ranging from about −196° C. to about −210° C. and is delivered into the cooling chamber 308 at that temperature at a constant flow rate to account for the drop in temperature of the liquid nitrogen within the cooling chamber 308 (as a result of heat absorbed from the helium passing through coil 328 at around room temperature). Thus, the helium enters the coiled tube 328 at about room temperature and exits the cooling chamber 308 at a temperature substantially equal to the temperature of the liquid nitrogen. Alternatively, the cooling chamber 308 need not be coupled to an insulated container 330 and instead simply contains a sufficient amount of liquid nitrogen at the appropriate temperature to ensure that the amount of cooling substrate to be used for one ablation procedure can be cooled to the appropriate temperature.

Alternatively, the cooling chamber 308 can be any known cooling device.

The cooled helium then passes along the cooling chamber output line 312D, through a bypass valve 336, through the ablation pad intake line 312E, and into the ablation chamber (not shown) of the ablation pad 302. After the helium passes through the channels within the ablation chamber in a continuous flow at a predetermined rate as discussed elsewhere herein, the helium flows out of the ablation chamber via the ablation pad output line 312G. It is understood that the ablation pad 302 can have any of the structures, features, or characteristics of any of the ablation pad embodiments disclosed or contemplated herein.

The system 300 also has a warm helium bypass line 312C. That is, once the ablation procedure is completed using the cooled helium that is provided as described above, warm helium is passed through the system—perhaps sourced from a cylinder 306—and directed at the bypass valve 326 into the warm helium bypass line 312C such that the warm helium does not pass through the cooling chamber 308. The warm helium passes through the bypass valve 336 into the ablation pad intake line 312E and thus into the pad 302. Alternatively, in certain implementations, the system 300 can also have a Joule Thomson restrictor (not shown) disposed along the warm helium bypass line 312C such that the helium passes through the restrictor (not shown) for further warming. The warm helium, according to one embodiment, is passed through the pad 302 to help thaw the ablation chamber of the ablation pad 302 and thus makes it possible for the ablation pad 302 to be removed from the target tissue by reversing the cryoadhesion via the warm helium.

It is understood that the ablation pad 302 can be any known ablation pad or device that can be coupled to the system 300. In certain implementations discussed elsewhere herein in additional detail, the pad 302 can have a multitude of channels in the ablation chamber (not shown) through which the gas can flow, including, according to certain embodiments, flowing continuously.

It is further understood that the cooling substrate in this system 300 can be another known substrate other than helium. For example, in one embodiment, the substrate is hydrogen.

In accordance with one implementation, the controller 310 is configured to be communicatively and operationally coupled to the various components of the system 300. That is, the controller 310 is configured to monitor the various components, such as, for example, the cooling chamber 308, the pad 302, and the various valves 316, 318, 326, 336, etc. Further, the controller 310 can also be configured to control those components. In one embodiment, the controller 310 has a graphic user interface ("GUI") incorporated therein that can be used by a user to monitor and control the various components of the system 300, including, in some examples, generation and display of voltage maps and/sensor data (not shown) that can be used to guide therapy.

Figure 24:
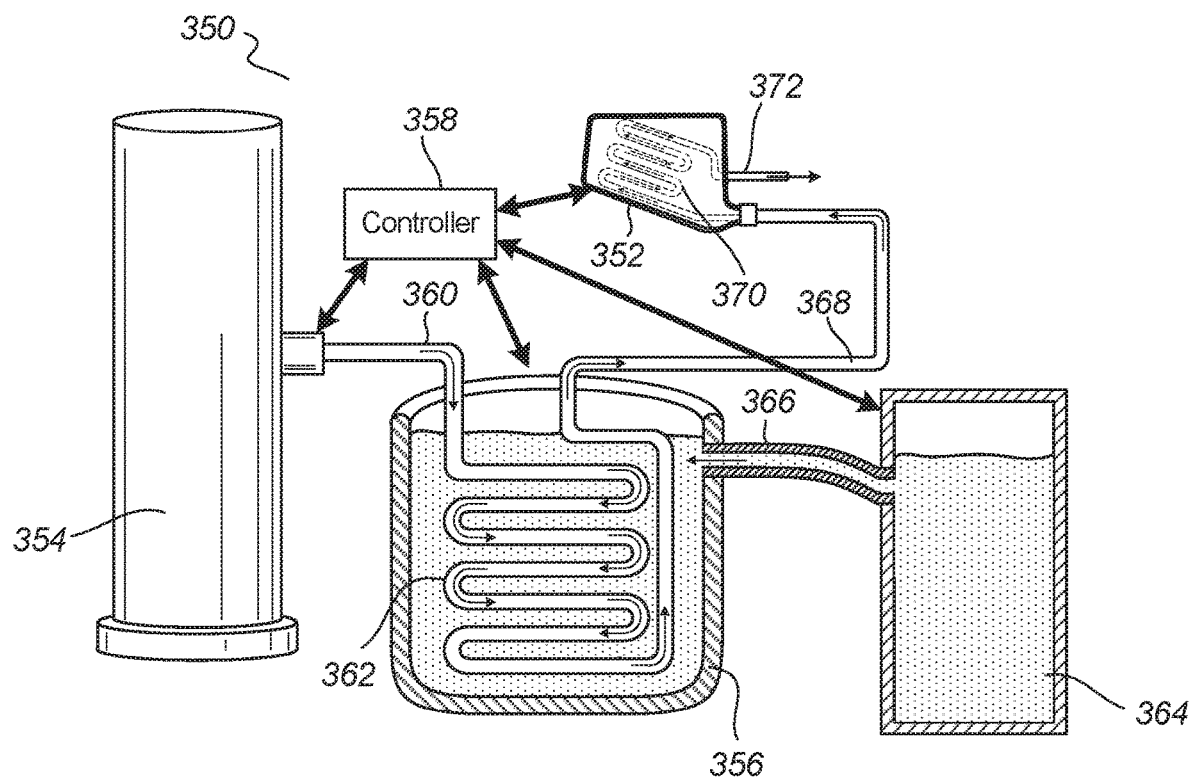
FIG. 24 is a schematic view of yet another ablation system, according to a further embodiment.
Figure 25:
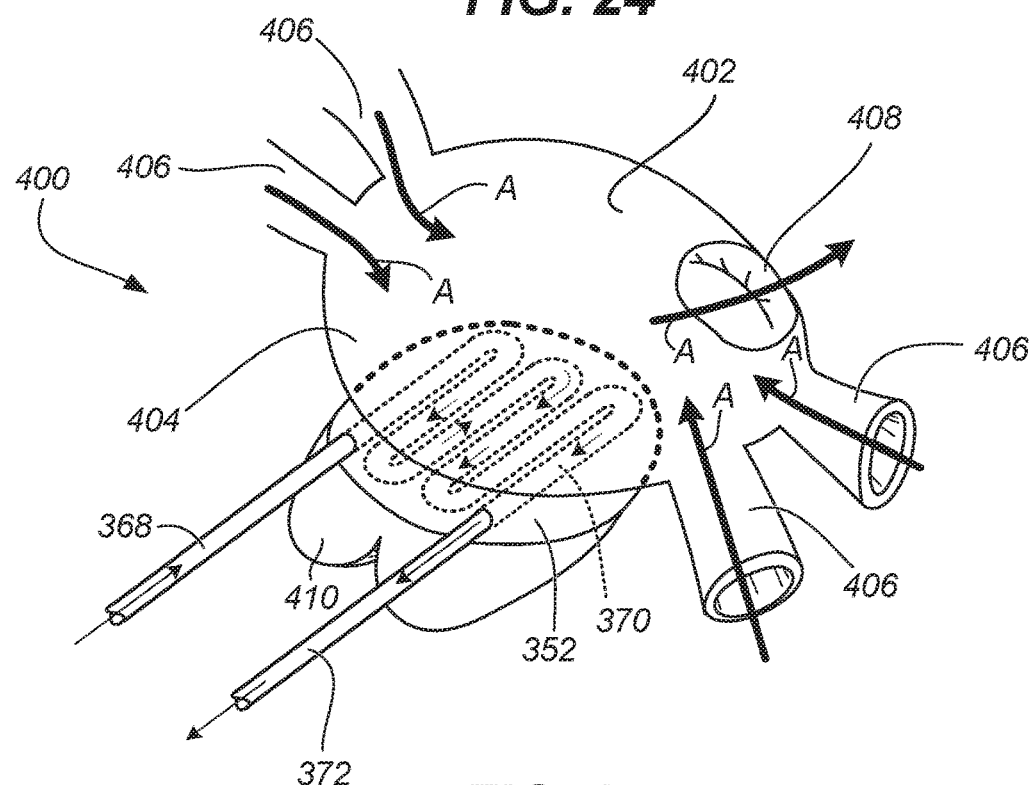
FIG. 25 is a perspective view of the ablation pad of FIG. 24 positioned against a patient's heart, according to one embodiment.
Figure 26:
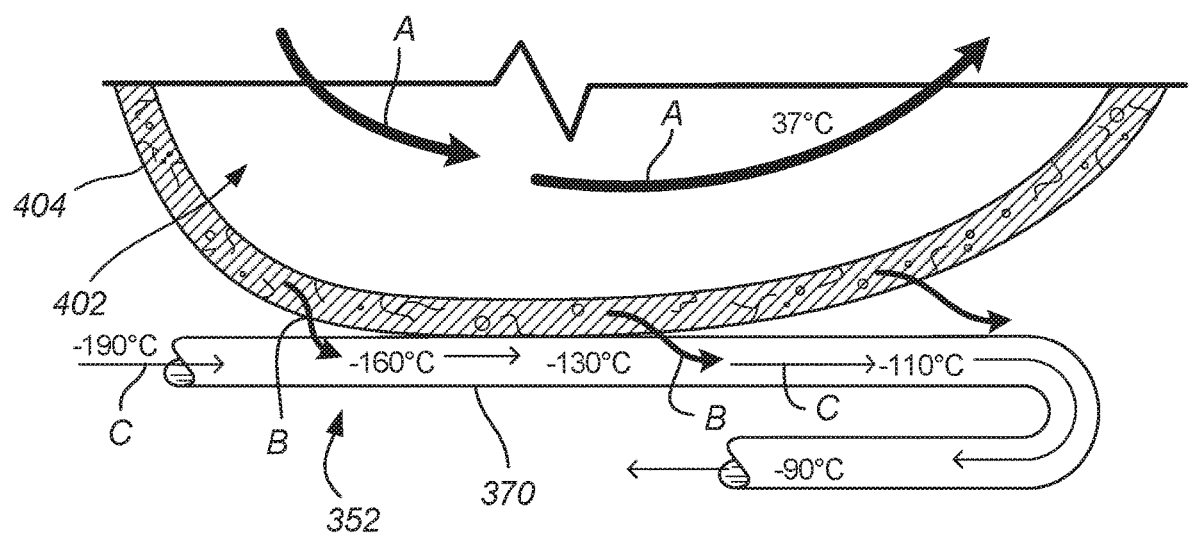
FIG. 26 is a side view of the ablation pad of FIG. 25 positioned against the patient's heart, according to one embodiment.

A further embodiment of an ablation system 350 is depicted in FIGS. 24-26. Like the system 300 discussed above with respect to FIG. 23, certain versions of this system 350 use helium as the cooling substrate. In certain implementations, helium is used because of its enhanced thermal conductivity in comparison with other known cryoablation gases such as argon, nitrous oxide, or nitrogen. The system 350 has an ablation pad 352, a pressurized cylinder of gas 354, a cooling (or "chilling") device 356, and a controller 358. And while they are not depicted in FIGS. 24-26, it is understood that the system 350 can have known check valves, sensors, and other appropriate standard components as described in additional detail in relation to the other system embodiments discussed elsewhere herein.

The pressurized cylinder of gas 354 provides the cooling substrate in the form of a gas. As mentioned above, in one specific embodiment, the gas is helium. Alternatively, the gas can be argon, nitrogen, or any other known gas that can be used as a cooling substrate. Further, the gas cylinders 354 can also provide a warming substrate in the form of a different gas to be supplied to the pad 352 after application of the cold gas. For example, the warming substrate can be helium or any other known warming substrate. Alternatively, the system 350 can have two or more cylinders.

In the specific implementation depicted in FIG. 24, the cylinder 354 contains helium (or any other known cooling substrate). In this embodiment, the helium flows from the cylinder 354 through a cooling substrate delivery line 360 to the cooling chamber 356. In this embodiment, the cooling chamber 356 has a coiled tube 362 disposed within a coolant within the chamber 356, such that the helium flows through the coiled tube 362. That is, the delivery line 360 is fluidically coupled to the coiled tube 362 (or the coiled tube 362 is an extension of, or integral part of, the delivery line 360) such that the helium flows along the delivery line 360 into the coiled tube 362 within the cooling chamber 356. It is understood that the tube 362 that is referred to as the coiled tube 362 is not coiled along its entire length in the chamber 365. Instead, at least a portion of the tube 362 length is coiled within the chamber 365 as shown, with non-coiled portions in the lengths extending from the delivery line 360 and toward the cooling chamber output line 368. In this specific implementation, the coolant is liquid nitrogen that flows from an insulated container 364 through a coolant delivery line 366 and into the chamber 356. As such, the helium flowing through the coiled tube 362 flows through the liquid nitrogen and is cooled as a result. That is, the temperature of the liquid nitrogen causes the temperature of the helium to drop, thereby resulting in the substantial cooling of the helium. In one specific embodiment, the liquid nitrogen is maintained in the insulated storage container 364 at a temperature ranging from about −196° C. to about −210° C. and is delivered into the cooling chamber 356 at that temperature at a constant flow rate to account for any drop in temperature of the liquid nitrogen within the cooling chamber 356. Thus, the helium enters the coiled tube 362 at about room temperature and exits the cooling chamber 356 at an extremely cold temperature according to some embodiments that is substantially equal to the temperature of the liquid nitrogen.

Alternatively, the cooling chamber 356 can be any known cooling device.

Upon exit from the cooling chamber 356, the cooled helium passes along the cooling chamber output line 368 and into the ablation chamber (not shown) of the ablation pad 352. After the helium passes through the channels 370 within the ablation chamber as discussed elsewhere herein, the helium flows out of the ablation chamber via the ablation pad output line 372.

It is understood that the ablation pad 352 can be any known ablation pad or device that can be coupled to the system 350. In certain implementations discussed elsewhere herein in additional detail, the pad 352 can have a multitude of channels in the ablation chamber (not shown) through which the cold gas can flow continuously in a unidirectional pathway for ablation.

In accordance with one implementation, the controller 358 is configured to be communicatively and operationally coupled to the various components of the system 350. That is, the controller 358 is configured to monitor the various components, such as, for example, the cooling chamber 356, the pad 352, etc. Further, the controller 358 can also be configured to control those components. In one embodiment, the controller 358 has a graphic user interface ("GUI") incorporated therein that can be used by a user to monitor and control the various components of the system 350, including, in some examples, generation and display of voltage maps that can be used to guide therapy.

FIG. 25 depicts the ablation pad 352 of FIG. 24 being positioned against the external wall 404 of the left atrium chamber 402 of a patient's heart 400. It is understood that the left atrium 402 receives blood that has traversed the rest of the patient's body and enters the left atrium 402 via the pulmonary veins 406. It is further understood that the blood is body temperature when it enters the left atrium 402: about 37° Celsius. As the heart 400 beats, this flow of blood is a continuous flow through the left atrium 402, through the mitral valve orifice 408, and into the left ventricle (not shown). The direction of this blood flow is indicated by arrows A as shown. This continual flow of warm blood from the patient's body works to keep the walls 404 warm.

As shown in FIG. 25, the pad 352 has a unidirectional channel or pathway 370 defined within the pad 352 such that ultra-cold helium gas can be delivered continuously at a predetermined flow rate via the cooling chamber output line 368 into the channel 370 within the pad 352 to ablate the outer muscle wall 404 via the direct contact between the pad 352 and the wall 404. In one embodiment, the gas flows continuously through the channel 370 and out of the pad 352 via the ablation pad output line 372. As the gas flows through the ablation pad 352, the gas draws heat from the atrial muscle wall 404, thereby warming the gas such that the gas exits the ablation pad 352 via the output line 372 at a higher temperature than when it entered the pad 352.

In one implementation, the pad 352 also has an insulation chamber 410 as shown. It is understood that the pad 352 can be any pad according to any embodiment as described elsewhere herein.

The heat transfer (and resulting ablation of the heart muscle wall 400) caused by the ablation pad 352 and coolant therein is depicted in further detail via a side, cross-sectional view in FIG. 26, according to one embodiment. More specifically, FIG. 26 depicts a side, cross-sectional view of the channel 370 of the ablation pad 352 in contact with the muscle wall 404 of the patient's heart 400. As indicated by the flow direction arrows A, warm, flowing blood is continuously flowing through the left atrium 402, thereby working to warm the left atrium chamber 402, including the muscle wall 404, and maintain an equilibrium temperature of around 37° C. At the same time, the unidirectional channel 370 in the ablation pad 352 allows for continuous flow of ultra-cold coolant gas at a predetermined rate through the channel 370 in the direction shown by arrows C, thereby cooling the muscle wall 404. In one embodiment, the coolant gas is helium. That is, as the coolant gas passes through the channel 370 while the pad 352 is in direct contact with the wall 404, heat is transferred from the wall 404 to the coolant gas as shown by arrows B such that the coolant gas is warmed as it passes through the channel 370. In accordance with one exemplary implementation as shown, the helium is delivered into the ablation pad 352 at around −190° C., and as the gas flows along the channel 370, it is gradually warmed via the heat transfer (represented by arrows B) as shown by the changing temperatures depicted in the figure such that the gas is around −90° C. when it exits the channel 370. This continuous flow of coolant gas passing therethrough must overcome the continuous heating action of the warm flowing blood within the left atrium chamber 402 in order to cool the heart wall 404. In one embodiment, the heat transfer (as shown by arrows B) to the thermally conductive cold gas draws heat from the muscle wall 404, thereby overcoming the heating action of the warm blood and cooling the muscle wall 404. In one embodiment, the ablation via the ablation pad 352 via the heat transfer as described herein cools the muscle wall 404 from around +37° C. to about −25° C. or colder. Alternatively, the wall 404 can be cooled to any temperature ranging from about −20° C. to about −45° C.

Thus, the various embodiments herein relate to ablation systems having ablation pads that can overcome both (1) the heating action of warm blood flowing through the heart chamber, (2) the insulating effect of fatty tissue covering various portions of the outer wall of the heart, and (3) the warming effect of blood flowing through blood vessels within the heart muscle tissue itself. Further, it is understood that any of the embodiments disclosed or contemplated herein can be used to ablate any external wall of any organ, including the posterior wall of the left atrium, the free wall of the right atrium, or segments of the ventricle. In certain implementations, the ablation pad is large enough to ablate an entire segment of an external surface of a tissue or organ (such as, for example, a heart chamber) with one application.

In certain embodiments, any of the ablation pad embodiments disclosed or contemplated herein can have one or more channels defined therein as described elsewhere such that the overall length of the channel/channels exceeds the length, width, or circumference of the pad. Further, the one or more channels can be disposed within a pad having a surface area that is substantially larger than the width of the individual channel(s). It is understood that, according to certain implementations, the channel walls attach to the opposing walls of the ablation chamber and thereby limit the height thereof, which can result in an external ablation chamber surface that is generally flat or slightly concave.

Figure 27:
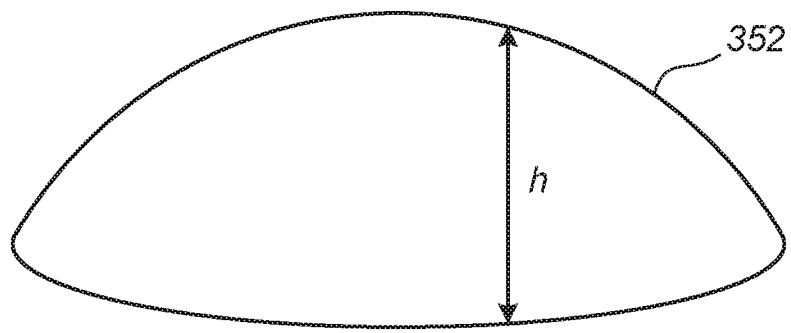
FIG. 27 is a side view of a known ablation pad or balloon.

As discussed above, it is understood that most known ablation devices, such as the known ablation device 352 in FIG. 27, have an inflatable balloon that, when pressurized with cold gas, tends to become spherical or bi-concave, with the height (h) of the ablation chamber increasing substantially. This configuration will decrease the thermal absorptive power of any cold gas circulating within the ablation chamber, with ablation 'power' being inversely proportional to chamber height (h) due to wasting or pooling of the cold gas.

Figure 28A:
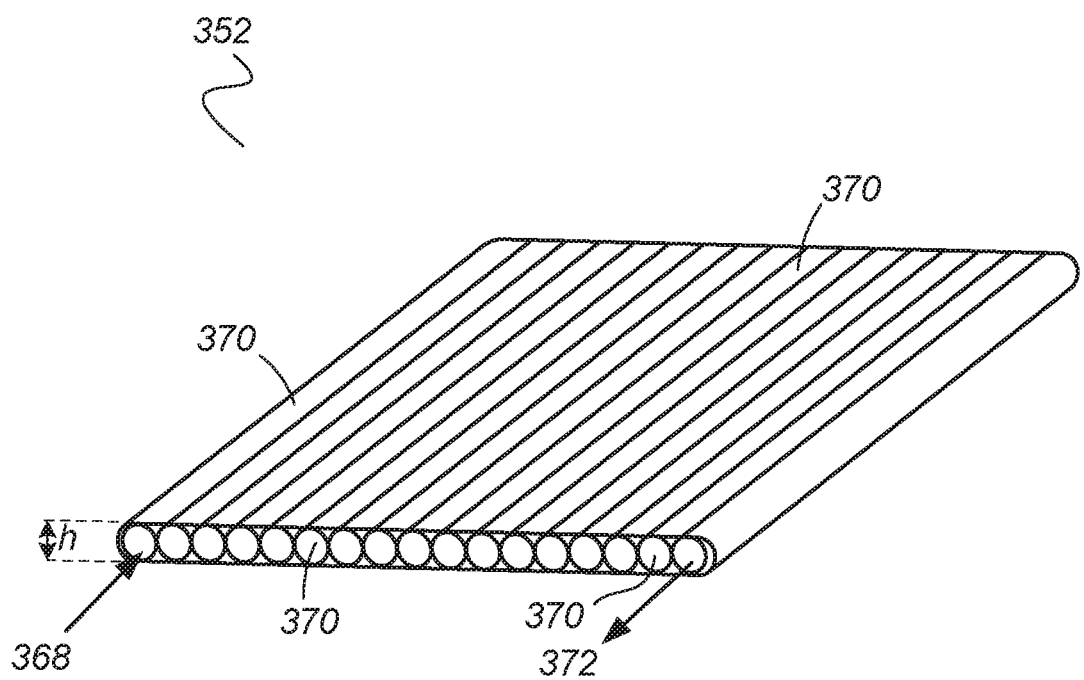
FIG. 28A is a perspective, cross-sectional view of an ablation device, according to one embodiment.
Figure 28B:
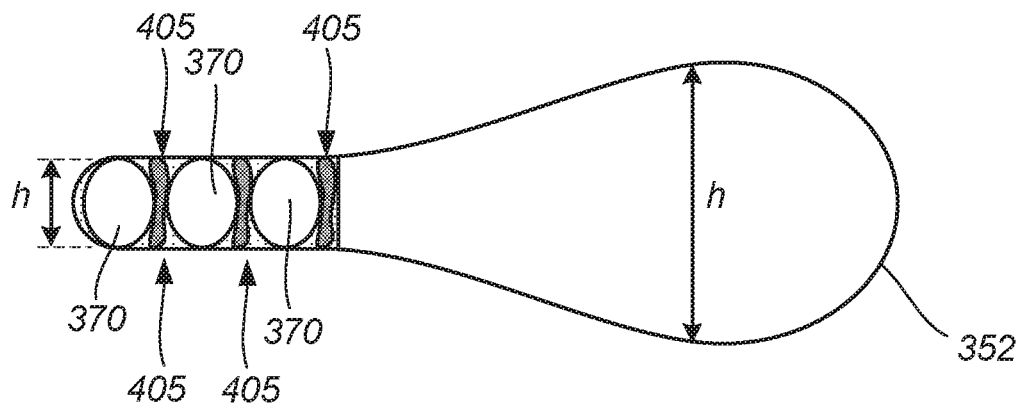
FIG. 28B is a side, cross-sectional view of the ablation device of FIG. 28A during construction, according to one embodiment.
Figure 28C:
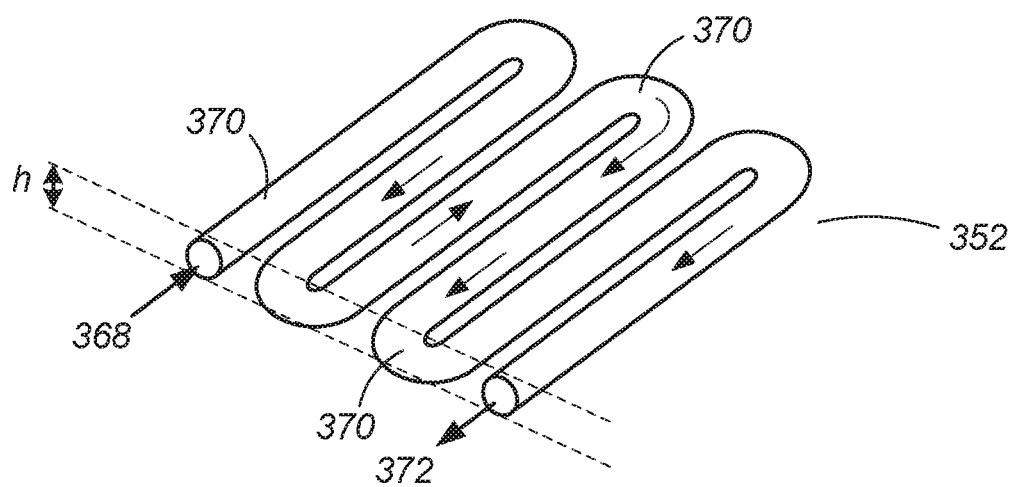
FIG. 28C is a perspective view of the channels of the ablation device of FIG. 28A, according to one embodiment.

In contrast, the ablation chamber implementations disclosed or contemplated herein maximize efficiency by minimizing the chamber height (h) while still allowing for gas flow through the chamber at the desired rate. For example, FIGS. 28A-28C depict perspective cross-sectional views of an ablation device 352, according to one embodiment. FIG. 28A depicts the entire device 352 with a series of channels 370 within the ablation pad 370 that minimize the height (h) substantially by sealing the top and bottom layers of the ablation chamber to one another along the channel 370 seal-lines, thereby eliminating this excess height. To further explain how the configuration of the device 352 minimizes the height (h) of the pad 370, FIG. 28B depicts a partially constructed device 352 according to one embodiment. This FIG. 28B shows how chamber height (h) is diminished substantially by the creation of channels 370, which are formed by welding lines 405 between the top and bottom layers of chamber 352. FIG. 28C provides another depiction of the device 352, and more specifically shows a series of undulating channels 370 of minimized height (h) with a unidirectional flow pathway (as shown with the arrows) from cold helium inlet line 368 to ablation pad outlet line 372. Of course, other pad and ablation chamber embodiments with unidirectional flow pathways are also contemplated herein.

Figure 29:
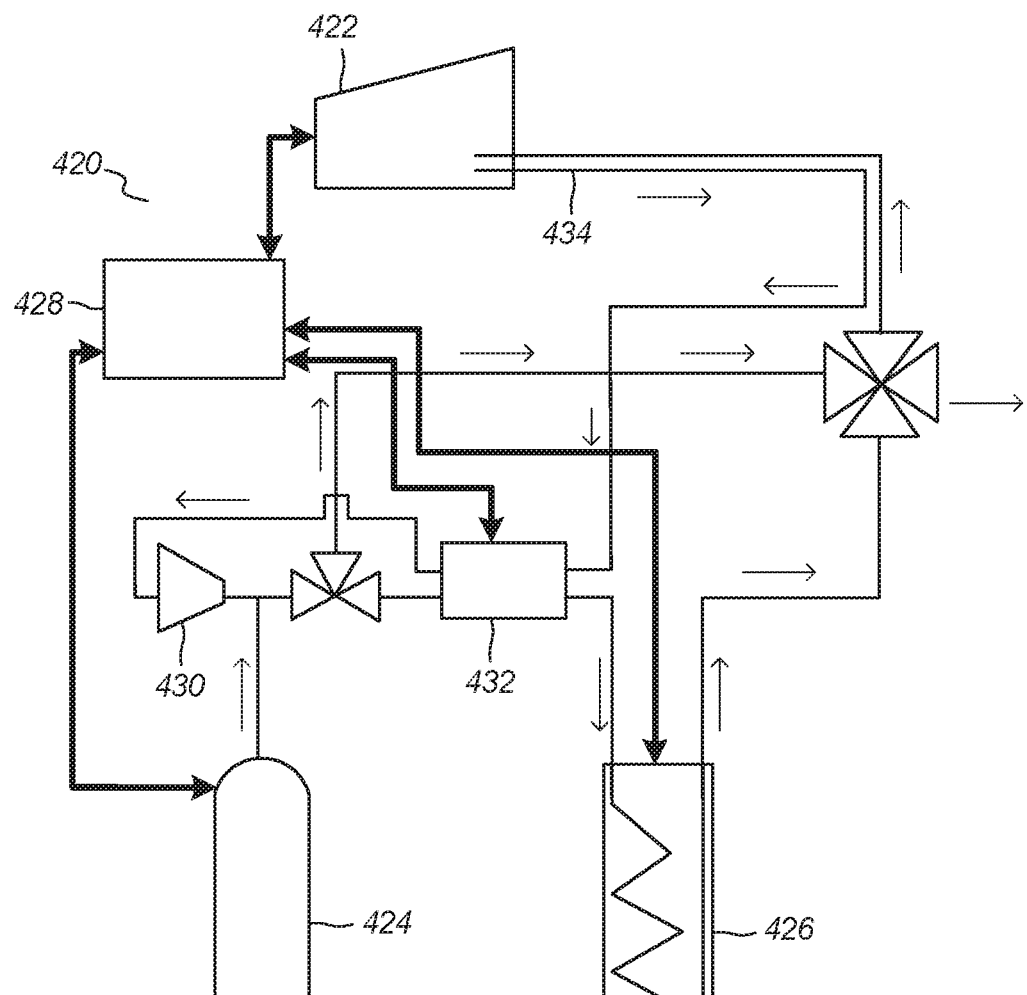
FIG. 29 is a schematic view of a further ablation system, according to another embodiment.

Another ablation system 420 implementation is depicted in FIG. 29. Like the previous system embodiments, this system 420 has a ablation pad 422, a pressurized cylinder of gas 424, a cooling (or "chilling") device 426, and a controller 428. It is understood that each of these components can have the features, components, and/or functionality of any equivalent component in the other system embodiments disclosed or contemplated herein. Further, the system 420 can operate in the same fashion as any of the other system embodiments disclosed or contemplated herein. In addition, while they are not depicted in FIG. 29, it is understood that the system 420 can also have known check valves, sensors, and other appropriate standard components as described in additional detail in relation to the other system embodiments discussed elsewhere herein. In certain embodiments, the cooling substrate in this system 420 is helium. Alternatively, it is another known substrate, such as hydrogen.

The system 420. in accordance with the embodiment as shown, is a closed-loop system 420 having a compressor (also referred to as a "recirculator") 430 that powers the recirculation of the cooling substrate and a pre-cooler (also referred to as a "recuperator" or "pre-cooling device") 432 that pre-cools the cooling substrate prior to the substrate being transported through the cooling device 426. In use, fresh cooling substrate exits the gas cylinder 424 and is urged by the compressor 430 through the pre-cooling device 432 and into the cooling device 426. In one embodiment, the pre-cooling device 432 cools the cooling substrate from room temperature to a pre-cooled temperature ranging from about −60° C. to about −100° C. Alternatively, the cooling substrate achieves a pre-cooled temperature of about −90° C. The pre-cooled substrate—at the pre-cooled temperature—then passes through the cooling device 426 and is cooled further prior to being transported to the ablation pad 422. After being urged through the ablation chamber (not shown) of the ablation pad 422, the cooling substrate exits the pad 422 via the output line 434 and is urged through the pre-cooling device 432. That is, the "spent" warmer cooling substrate from the pad 422—which is still very cold in comparison to the cooling substrate prior to entering the cooling chamber 426—is used as the pre-cooling coolant in the pre-cooling device 432 to pre-cool the cooling substrate passing through the pre-cooler 432 prior to entering the cooling device 426, as described above. In one embodiment, the spent cooling substrate has a temperature ranging from about −60° C. to about −100° C., which explains the resulting temperature of the pre-cooled substrate prior to entering the cooling device 426. The spent cooling substrate is then transported from the pre-cooler 432 to the compressor/recirculatory 430, which urges the cooling substrate to cycle back to the beginning of the process. That is, the compressor 430 urges the cooling substrate through the pre-cooler 432 to be pre-cooled prior to entering the cooling device 426 and then being urged through the ablation chamber (not shown) of the pad 422 again. As discussed above, the closed-loop configuration of this system 420 conserves the cooling substrate through re-use, rather than simply venting the cooling substrate and requiring 100% of the additional cooling substrate be new substrate that hasn't already passed through the system 422.

The pre-cooler 432, according to various embodiments, is a heat-exchange device that allows for heat to be transferred from the cooling substrate to the "spent" or warmed cooling substrate as the cooling substrate is advancing toward the cooler 426 and the spent cooling substrate is coming from the ablation pad 422. More specifically, the pre-cooler 432 has first conduit (also referred to as a "fresh substrate conduit" or "cooling substrate conduit") (not shown) and a second conduit (also referred to as a "spent substrate conduit" or "warmed cooling substrate conduit") (not shown) that pass in close proximity to each other within the pre-cooler 432. It is understood that the "warmed substrate" language is misleading, because the spent substrate from the pad 422 is still much colder than the "fresh" substrate that is being advanced toward the cooler 426. Regardless, as the cooling substrate passes through the cooling substrate conduit and the spent substrate passes through the spent substrate conduit, the cooling substrate is cooled as described above to a temperature in a range from about −60° C. to about −100° C. It is understood that any known heat exchange device allowing for the transfer of heat from one fluid to another in a similar environment can be used herein.

In one embodiment the compressor 430 is a Model CAT-4620 AC compressor, which is commercially available from California Compressor. Alternatively, any known compressor for use in similar ablation or medical device systems can be used. In a further alternative, the compressor 430 can be any type of pump or fluid driver that can be used in such a system for driving fluid through the system.

It is understood that the system 420 is a closed-loop system such that the cooling substrate can be reused rather than intentionally vented from the system. Thus, initial operation of the system 420 involves the "fresh" cooling substrate originating from the tank 424 and then passing through the cooler 426 and into the pad 422. There is no pre-cooling step at this point, because there is no spent cooling substrate passing through the pre-cooler 432. Thus, the fresh cooling substrate from the tank 424 can either pass through the pre-cooler 432 with no pre-cooling effect taking place, or the fresh substrate can bypass the pre-cooler 432. When the cooling substrate advances through the pad 422 and begins to warm as described above and elsewhere herein, it becomes "spent" cooling substrate as it exits the pad 422 and is advanced to the pre-cooler 432. As the spent substrate passes through the spent substrate conduit, it begins to cool the fresh substrate passing through the cooling substrate conduit. The spent cooling substrate then advances to the compressor 430, which drives the cooling substrate back toward the pre-cooler 432. At this point, the cooling substrate has reached the end of the closed loop and is now at the beginning again such that it constitutes cooling substrate that will be advanced through the pre-cooler 432, where it will be pre-cooled and then advanced into the cooler 426 as described elsewhere herein. The cooling substrate continues to pass through the closed-loop cycle of the pre-cooler 432 (as cooling substrate that is pre-cooled), the cooler 426, the ablation pad 422, back through the pre-cooler 432 (as spent cooling substrate that is used to pre-cool the cooling substrate passing through the first conduit), and then through the compressor 430 and thus back to the beginning of the loop. In certain embodiments, once the closed-loop has sufficient amounts of the cooling substrate in the loop, the flow of fresh cooling substrate from the tank 424 is stopped, and additional fresh substrate is only provided as small amounts of cooling substrate in the loop are lost to leakage and the like.

Figure 30:
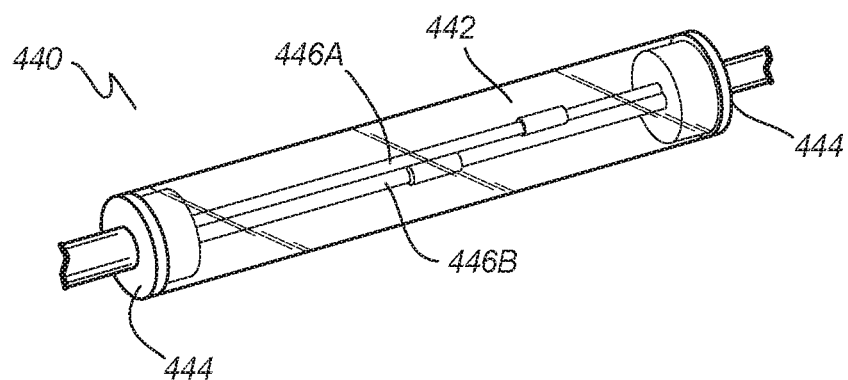
FIG. 30 is a perspective view of an insulation tube, according to one embodiment.
Figure 31:
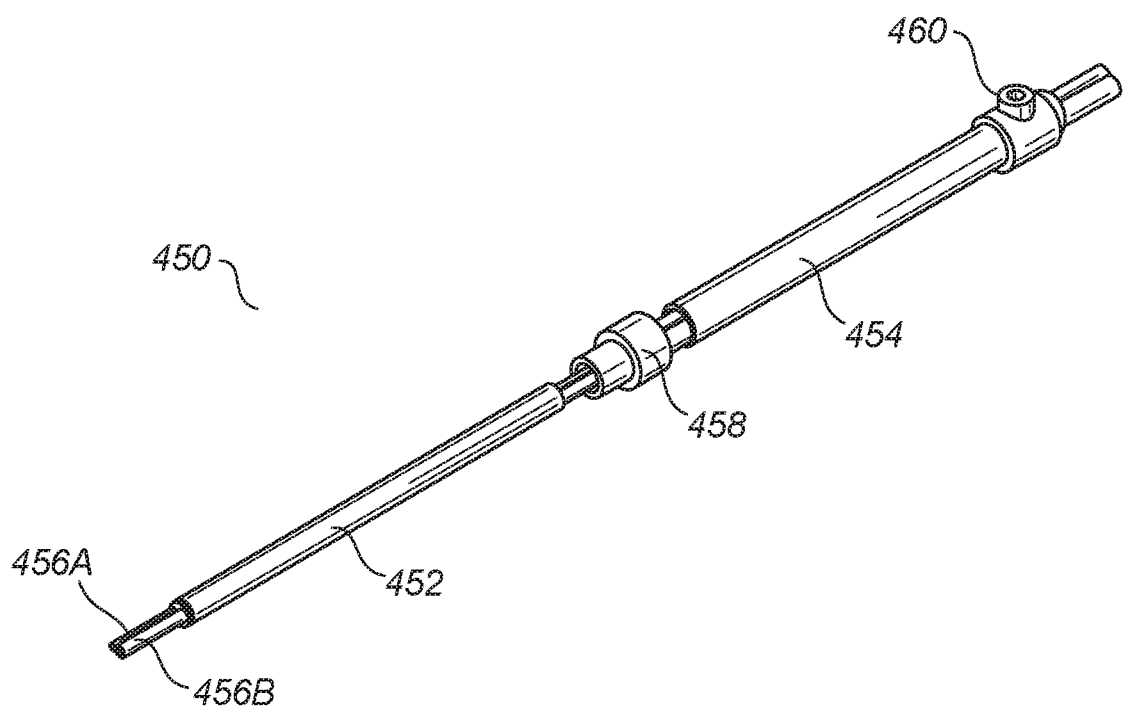
FIG. 31 is a perspective view of an insulation tube set, according to another embodiment.

In accordance with various embodiments as depicted in FIGS. 30 and 31, any system embodiment as disclosed or contemplated herein (including system 100, system 300, system 350, or system 420) can have an outer tube (also referred to herein as an "encasing tube," "insulation tube," "vacuum tube," "insulation jacket," or "vacuum jacket") 440 disposed around one or more system substrate lines (or tubes) 446A, 446B. The tube, as best shown in FIG. 30, has a tube body 442 and end caps 444 coupled at each end of the body 442 in a fluidically sealed fashion such that the interior of the body 442 is fluidically sealed in relation to the ambient air external to the tube 440. As such, the body 442 and end caps 444 are coupled to allow a vacuum to be created within the interior of the fluidically sealed tube 440. In this implementation, the outer tube 440 is disposed around two substrate lines 446A, 446B of an ablation system according to any of the embodiments herein. For example, the lines 446A, 446B can be a substrate inlet line 446A and a substrate outlet line 446B. Alternatively, the lines 446A, 446B can be any lines provided in such an ablation system. In a further alternative, the tube 440 can be disposed around one line, three lines, or any number of lines in an ablation system. Further, in one embodiment, the outer tube 440 can be disposed around the substrate line(s) 446A, 446B along their entire length from one system component (such as, for example, the source gas canister) to another (such as, for example, the ablation pad). Alternatively, the tube 440 can be disposed along any length of such line(s) 446A, 446B.

The end caps 444 as shown have fluidically sealable openings defined therethrough that are configured to receive the lines 446A, 446B and allow the lines 446A, 446B to pass through while maintaining the vacuum therein. Further, it is also understood that instead of one or both of the end caps 444, one or both of the ends of the body 442 of the tube 440 could instead be coupled to or integral with one or more of the components in the system (according to any system embodiment herein) into which the line(s) 446A, 446B extend such that the fluidic seal is maintained in the interior of the tube 440.

Continuing with FIG. 30, a vacuum is applied to the space or interior defined within the outer tube 440. That is, the air pressure within the interior of the tube 440 is reduced in comparison to the ambient air outside the tube 440. In one embodiment, a pump (not shown in FIG. 30) is coupled to the tube 440 and is configured to create the vacuum. Any known pump 406 for use in creating a vacuum can be used. When the vacuum is created, the outer tube 440 and the vacuum applied to the interior thereof insulates the lines 446A, 446B. That is, the outer tube 440 and the vacuum provide a powerful insulator that is strong enough to insulate the extreme temperatures of the lines 446A, 446B resulting from the ultracold substrates passing therethrough with temperatures as described elsewhere herein. In one embodiment, the outer tube 440 insulates the lines 446A, 446B such that the insulation reduces the amount of warming of the cooling substrate that occurs as the substrate moves along the line(s) 446A, 446B. As such, the outer tube 440 and vacuum prevent or minimize warming of the cooling substrate. Further, the outer tube 440 and vacuum can also protect users from serious injury as a result of touching the ultra-cold substrate line(s) 446A, 446B by providing an outer tube 440 with a vacuum such that the external surface of the tube 440 has a temperature above 32° F., such that a user can touch it without injury.

A set of outer tubes 450 is depicted in FIG. 31, according to another embodiment. In this implementation, the insulation tube set 450 includes a smaller tube 452 and a larger tuber 454, wherein the larger tube 454 has a larger diameter than the smaller tube 452. In this embodiment, the tubes 452, 454 are disposed around two substrate lines 456A, 456B, with one being the substrate inlet line 456A and one being the substrate outlet line 456B. It is understood that these outer tubes 452, 454 can have the same features and characteristics as the tube 440 discussed above except as explained otherwise herein. The tube set 450 also has a tube coupler 458 and a port 460. The tube coupler 458 in this specific embodiment couples the smaller tube 452 to the larger tube 454. Alternatively, a coupler (potentially similar to the coupler 448) could be used to couple a tube (such as either tube 452, 454) to a component of an ablation system into which the lines 446A, 446B extend.

The port 460, according to one embodiment, provides fluidic access to the interior of the tubes 452, 454 such that a pump (not shown) can be coupled to the port 460 to apply the vacuum to the interior of those tubes 452, 454.

It is understood that similar couplers (similar to coupler 458) and ports (similar to port 460) can be used with outer tube 440 as described above as well.

It is understood that the outer tube (such as outer tubes 440, 452, or 454) and equivalent terms as used herein are intended to mean any encasement structure that can be disposed around one or more substrate lines (or receive one or more such lines therein) and be fluidically sealed such that a vacuum can be created within the interior of the fluidically sealed tube 440.

Helium can be used as the coolant substrate in any of the embodiments disclosed or contemplated herein. Helium has an order of magnitude higher thermal conductivity than most other gases This property means that helium can absorb or release heat much more efficiently (on the order of 10×) than other more commonly used gases in clinical ablation devices such as argon or nitric oxide. Helium can be compressed and cooled in liquid form, or be cooled in a dewar filled with liquid nitrogen or nitrogen slush by running room temperature helium through a coil immersed in the liquid nitrogen or other very cold liquid.

In certain alternative embodiments, the insulation chamber of any pad disclosed or contemplated herein can have a volume of a gas with poor thermal conductivity (such as argon or air, for example).

Examples

Two different gases were tested as the coolant substrate for an ablation system similar to the systems described herein. More specifically, argon and helium were tested as the coolant substrate in two separate tests. In each test, the specific gas was delivered into the ablation channel with continuous flow at a temperature ranging from about −150° C. to about −190° C.

The argon coolant was tested in an ablation system in which the surface to be ablated was warmed (in a fashion similar to the flowing blood in a heart chamber) with a warm water flow rate of 2 L per minute, which caused the tissue contacted by the ablation pad to cool to −2° C. Assuming a simulated blood flow rate of 5 L/min (which replicates the actual flow rate in the human heart), it is estimated that the argon coolant would only cool the tissue to a temperature that is warmer than about −2° C.

The helium coolant was tested in the same ablation system in which the surface to be ablated was warmed with a warm water flow rate of 5 L/minute, which caused the tissue to cool to −45° C.

The results show that helium has an enhanced ability to absorb heat (and thereby cool tissue) in comparison to the other two gases.

Although the present invention has been described with reference to preferred embodiments, persons skilled in the art will recognize that changes may be made in form and detail without departing from the spirit and scope of the invention.

What is claimed is:

1. A system for ablating a generally planar surface of tissue, the system comprising an ablation component comprising:
   (a) a first chamber defined in the ablation component, the first chamber comprising:
      (i) an intake port operably coupled to the first chamber;
      (ii) an outlet port operably coupled to the first chamber;
      (iii) a single unidirectional fluid pathway defined by a channel disposed along an external wall in the first chamber and in fluid communication with the intake and outlet ports; and
      (iv) channel walls defining the channel;
   (b) an inflatable second chamber defined in the ablation component, wherein the second chamber is a low thermal conductivity chamber; and
   (c) an ablation fluid continuously flowable through the channel at a flow rate of at least about 80 liters per minute,
   wherein the channel walls are attached to the external wall and an internal wall such that the external wall is flat while the ablation fluid is flowing through the channel at the flow rate of at least about 80 liters per minute.

2. The system of claim 1, wherein the ablation fluid is helium gas that is sufficiently cold to ablate target tissue.

3. The system of claim 1, wherein the ablation fluid has a temperature lower than about −150° Celsius at the intake port.

4. The system of claim 1, wherein the ablation fluid has a pressure that is less than or equal to about 40 psi.

5. The system of claim 1, wherein the second chamber is configured to be capable of insulating tissue adjacent to the target tissue during an ablation procedure.

6. The system of claim 1, wherein a length of the fluid pathway is greater than a perimeter length of the first chamber.

7. The system of claim 1, wherein the first chamber comprises at least one baffle wall disposed within the channel.

8. A system for ablating a generally planar surface of tissue, the system comprising an ablation component comprising:
   (a) a first chamber defined in the ablation component, the first chamber comprising:
      (i) an intake port operably coupled to the first chamber;
      (ii) an outlet port operably coupled to the first chamber; and
      (iii) a single predetermined unidirectional fluid pathway extending through a single conduit disposed within the first chamber from the intake port to the outlet port; and
      (iv) channel walls attached to an external wall and an internal wall of the first chamber such that the channel walls prevent expansion of the external wall in relation to the internal wall when a fluid is urged through the single conduit;
   (b) an inflatable second chamber defined in the ablation component, wherein the second chamber is a low thermal conductivity chamber; and
   (c) an ablation fluid continuously flowable through the conduit at a flow rate of at least about 80 liters per minute,
   wherein the external wall is flat while the ablation fluid is flowing through the channel at the flow rate of at least about 80 liters per minute as a result of the channel walls.

9. The system of claim 8, wherein the ablation fluid has a temperature lower than about −150° Celsius at the intake port.

10. The system of claim 8, wherein the ablation fluid is helium gas that is sufficiently cold to ablate the target tissue.

11. The system of claim 8, wherein the second chamber is configured to be capable of insulating tissue adjacent to the target tissue during an ablation procedure.

12. The system of claim 8, wherein the ablation component comprises a collapsed configuration and a deployed configuration.

13. The system of claim 1, wherein the flow rate is at least about 120 liters per minute.

14. The system of claim 8, wherein the flow rate is at least about 120 liters per minute.

15. A system for ablating a generally planar surface of tissue, the system comprising an ablation component comprising:
   (a) a first chamber defined in the ablation component, the first chamber comprising:
      (i) a chamber body comprising an external wall, an internal wall, sides attached to the external wall and the internal wall, and an interior defined by the external wall, the internal wall, and the side;
      (ii) an intake port operably coupled to the first chamber body;

(iii) an outlet port operably coupled to the first chamber body; and
(iv) channel walls disposed within the interior, wherein the channel walls are attached to the external wall and the internal wall such that the channel walls define a channel comprising a single unidirectional fluid pathway disposed along the external wall in the interior and in fluid communication with the intake and outlet ports;
(b) an inflatable second chamber defined in the ablation component, wherein the second chamber is a low thermal conductivity chamber; and
(c) an ablation fluid continuously flowable through the channel at a flow rate of at least about 80 liters per minute,
wherein the external wall is flat while the ablation fluid flows through the channel at the flow rate of at least about 80 liters per minute.

16. The system of claim 15, wherein the internal wall is flat while the ablation fluid flows through the channel at the flow rate of at least about 80 liters per minute.

17. The system of claim 15, wherein the ablation fluid has a temperature lower than about −150° Celsius at the intake port.

18. The system of claim 15, wherein the ablation fluid is helium gas that is sufficiently cold to ablate the target tissue.

19. The system of claim 15, wherein the second chamber is configured to be capable of insulating tissue adjacent to the target tissue during an ablation procedure.

20. The system of claim 15, wherein the ablation component comprises a collapsed configuration and a deployed configuration.

* * * * *